(12) United States Patent
Leclerc et al.

(10) Patent No.: US 9,095,537 B2
(45) Date of Patent: Aug. 4, 2015

(54) THERAPY OF CANCER BASED ON TARGETING ADAPTIVE, INNATE AND/OR REGULATORY COMPONENT OF THE IMMUNE RESPONSE

(75) Inventors: Claude Leclerc, Paris (FR); Pedro Berraondo Lopez, Pamplona (ES)

(73) Assignees: INSTITUT PASTEUR, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 1306 days.

(21) Appl. No.: 11/778,267

(22) Filed: Jul. 16, 2007

(65) Prior Publication Data

US 2008/0152665 A1 Jun. 26, 2008

Related U.S. Application Data

(60) Provisional application No. 60/879,333, filed on Jan. 9, 2007.

(30) Foreign Application Priority Data

Sep. 1, 2006 (EP) ..................... 06291393

(51) Int. Cl.
| | |
|---|---|
| A61K 39/10 | (2006.01) |
| A61K 39/00 | (2006.01) |
| A61K 39/12 | (2006.01) |
| C07K 14/005 | (2006.01) |
| C12N 7/00 | (2006.01) |
| C12N 9/88 | (2006.01) |

(52) U.S. Cl.
CPC ............ *A61K 39/0011* (2013.01); *A61K 39/12* (2013.01); *C07K 14/005* (2013.01); *C12N 7/00* (2013.01); *C12N 9/88* (2013.01); *A61K 39/00* (2013.01); *A61K 2039/555* (2013.01); *A61K 2039/55511* (2013.01); *A61K 2039/55516* (2013.01); *A61K 2039/55561* (2013.01); *A61K 2039/70* (2013.01); *C07K 2319/00* (2013.01); *C07K 2319/01* (2013.01); *C07K 2319/33* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 5,952,303 A | 9/1999 | Bornstein | |
| 6,534,062 B2 * | 3/2003 | Raz et al. | 424/193.1 |
| 6,673,914 B1 | 1/2004 | Hoon | |
| 8,628,779 B2 | 1/2014 | Preville | |
| 8,637,039 B2 | 1/2014 | Preville | |

FOREIGN PATENT DOCUMENTS

| | | |
|---|---|---|
| EP | 1576967 B1 | 12/2007 |
| WO | 2005053738 A1 | 6/2005 |
| WO | WO 2005089792 A1 * | 9/2005 |
| WO | 2008026071 A2 | 3/2008 |
| WO | 2008026071 A3 | 3/2008 |

OTHER PUBLICATIONS

Dadaglio, G., et al. International Immunology, 15(12): 1423-1430, 2003.*
Lutsiak, M.E.C., et al. Blood, 105(7): 2862-2868, 2005.*
Heckelsmiller et al (Journal of Immunology, 2002, 169:3892-3899).*
Taieb et al (Journal of Immunology, 2006, 176:2722-2729; published Mar. 1, 2006).*
Krieg et al (Current Oncology Reports, 2004, 6:88-95).*
Takeda et al (Annual Review of Immunology, 2003, 21:335-376).*
Office Action dated Jan. 14, 2010 in U.S. Appl. No. 11/517,313.
Office Action dated Apr. 19, 2011 in U.S. Appl. No. 12/439,379.
Office Action mailed Jun. 10, 2014 in U.S. Appl. No. 12/439,379.
Office Action mailed Mar. 29, 2012 in U.S. Appl. No. 12/439,379.
Office Action mailed Sep. 29, 2011 in U.S. Appl. No. 12/439,379.
Pashine, Achal, et al., Nature Medicine Supplement, vol. 11, No. 4, pp. S63-S68 (2005).
Preville, Xavier, et al., Cancer Research, vol. 65, pp. 641-649 (2005).
Vierboom, Michel P.M., et al., Int. J. Cancer, vol. 87, pp. 253-260 (2000).
Stills, Harold F., ILAR Journal, vol. 46, No. 3, pp. 280-293 (2005).

* cited by examiner

*Primary Examiner* — Misook Yu
*Assistant Examiner* — Julie Wu
(74) *Attorney, Agent, or Firm* — Law Office of Salvatore Arrigo and Scott Lee, LLP

(57) ABSTRACT

The invention relates to a kit of parts, suitable for use in a therapy of cancer, wherein said kit comprises:
(i) a recombinant protein comprising one or several polypeptides bearing one or several epitopes of one or several tumor-associated antigens, said polypeptides being inserted in the same or different permissive sites of an adenylate cyclase (CyaA) protein or of a fragment thereof, wherein said CyaA fragment retains the property of said adenylate cyclase protein to target Antigen Presenting Cells or a mixture of such recombinant proteins wherein at least one of said epitopes, or tumor associated antigens, or insertion sites of CyaA protein, or fragment of said CyaA protein is different between the various recombinant proteins in the mixture; and said kit of parts further comprises at least one of the following compounds;
(ii) an agent, suitable for modulating a regulatory immune response in a patient ad optionally;
(iii) an adjuvant component suitable for activating the innate immune response in a patient.

32 Claims, 21 Drawing Sheets

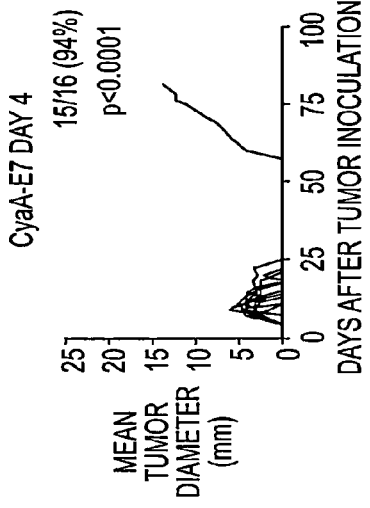
FIG. 1.1B
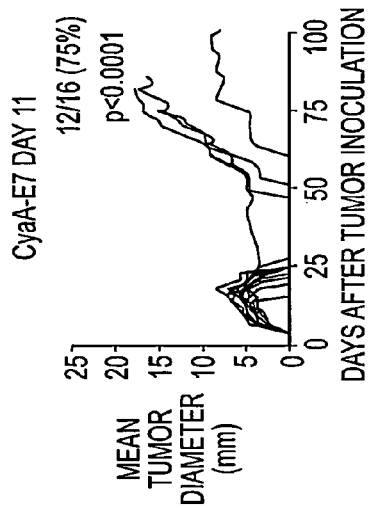
FIG. 1.1D
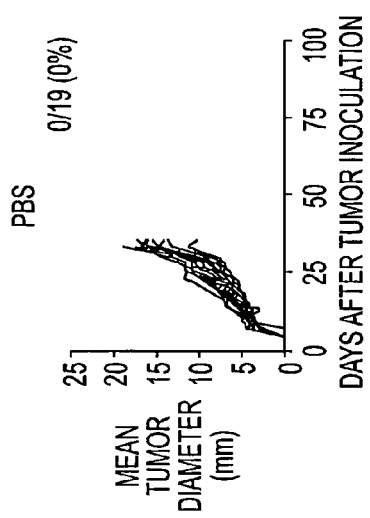
FIG. 1.1A
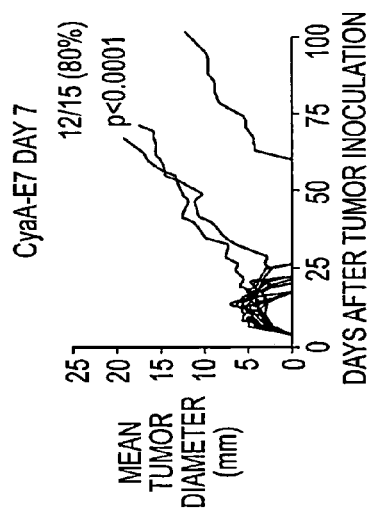
FIG. 1.1C

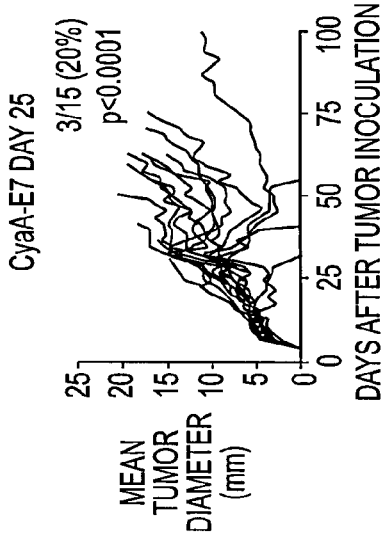
FIG. 1.1E
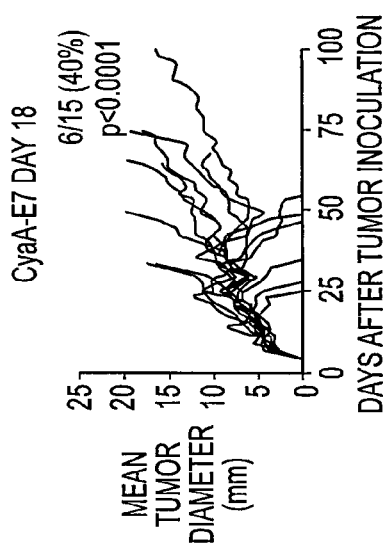
FIG. 1.1G
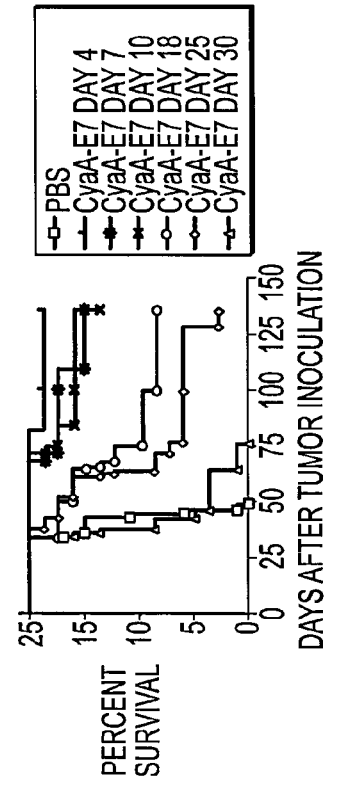
FIG. 1.1F
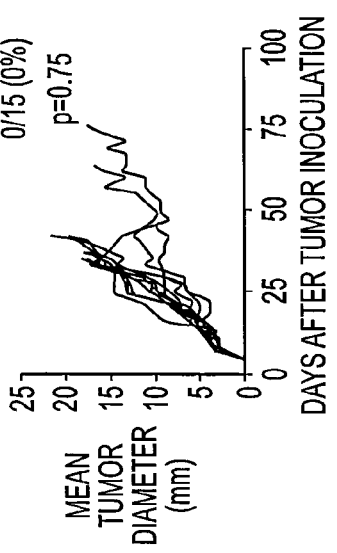
FIG. 1.1H

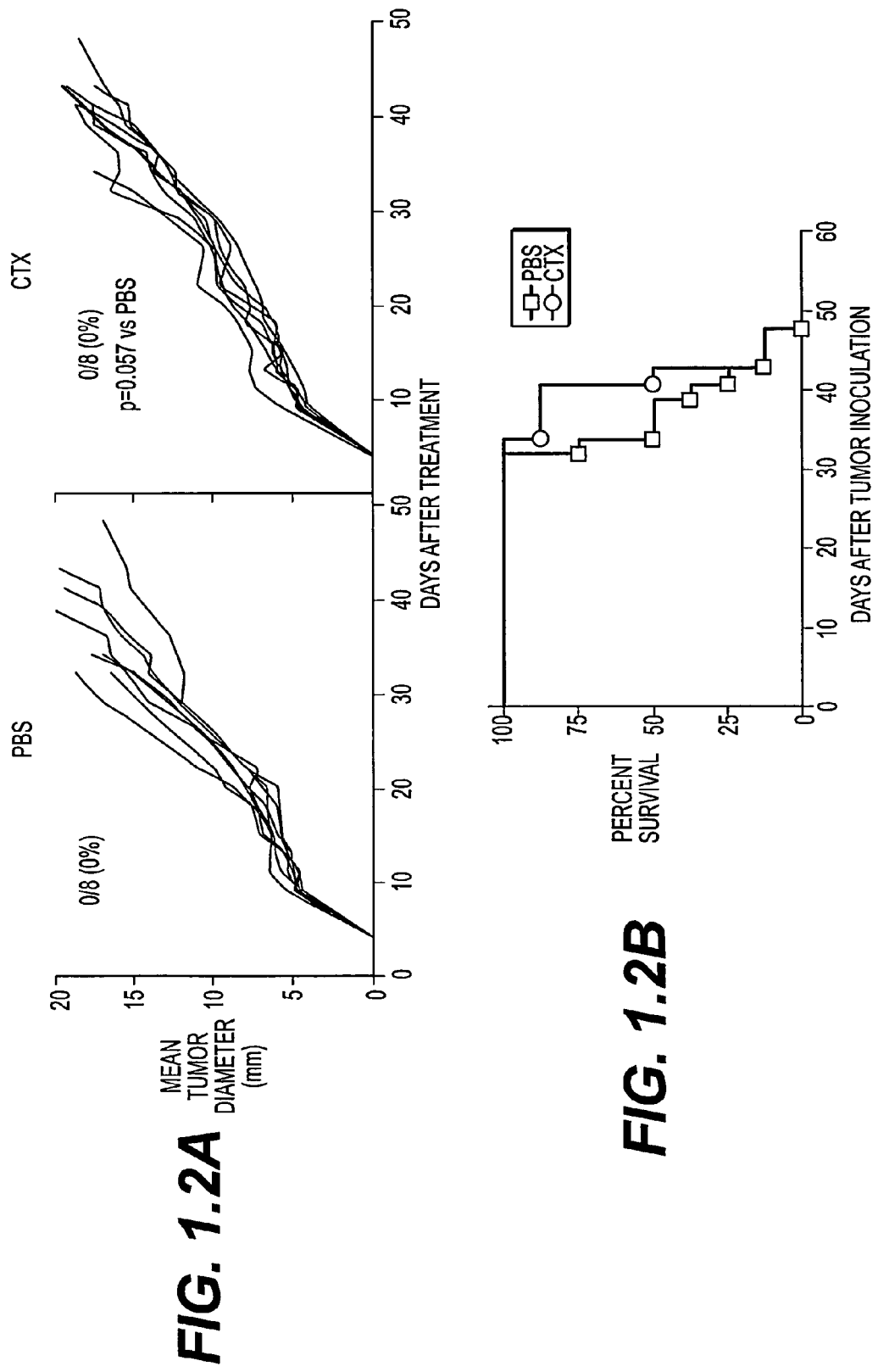
FIG. 1.2A
FIG. 1.2B

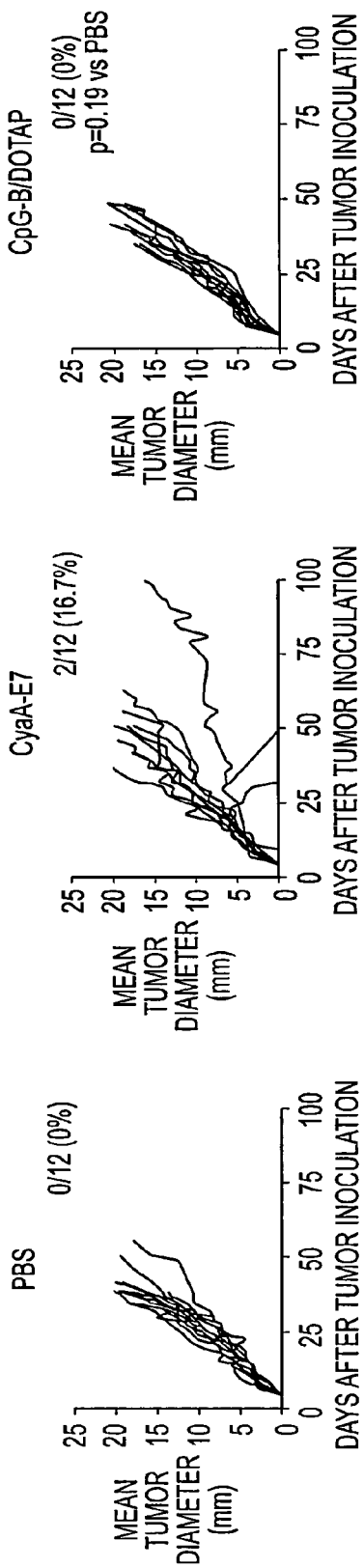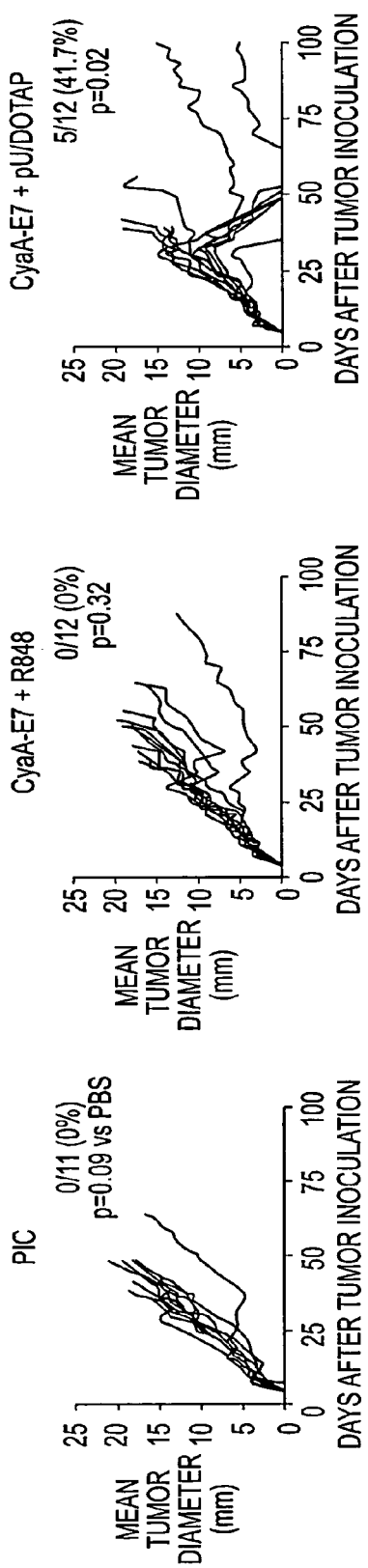

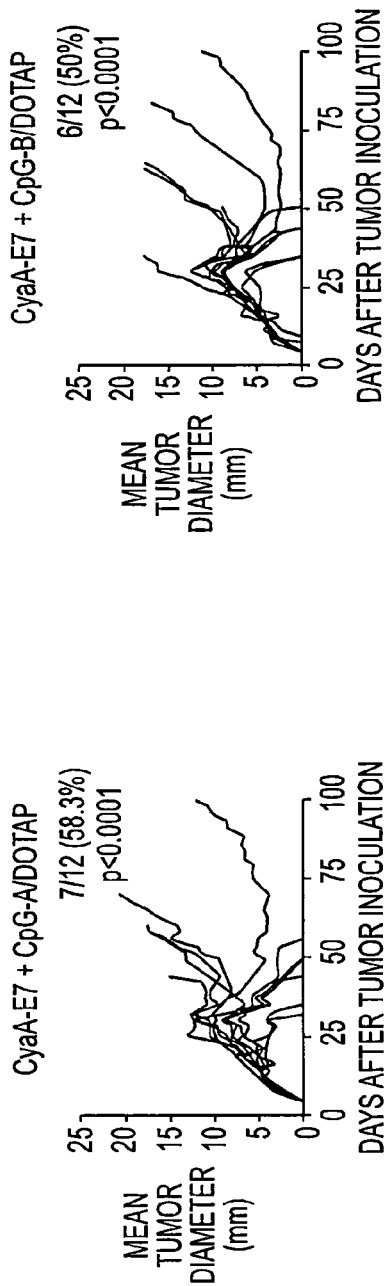
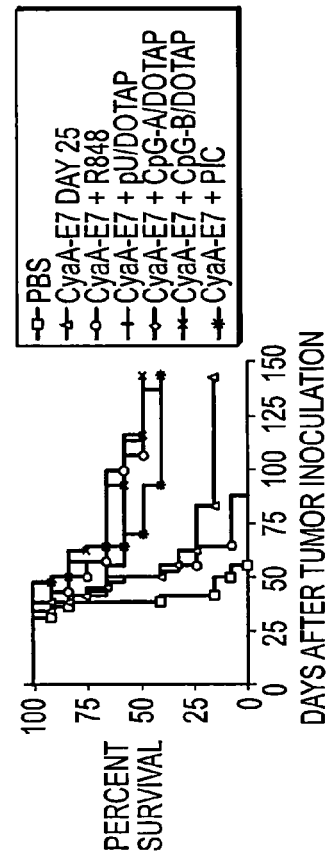
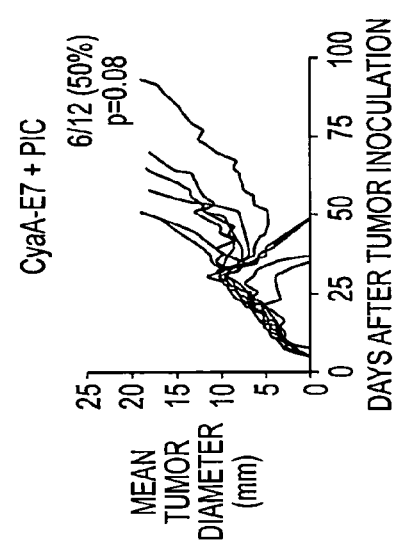
FIG. 2.1H
FIG. 2.1J
FIG. 2.1G
FIG. 2.1I

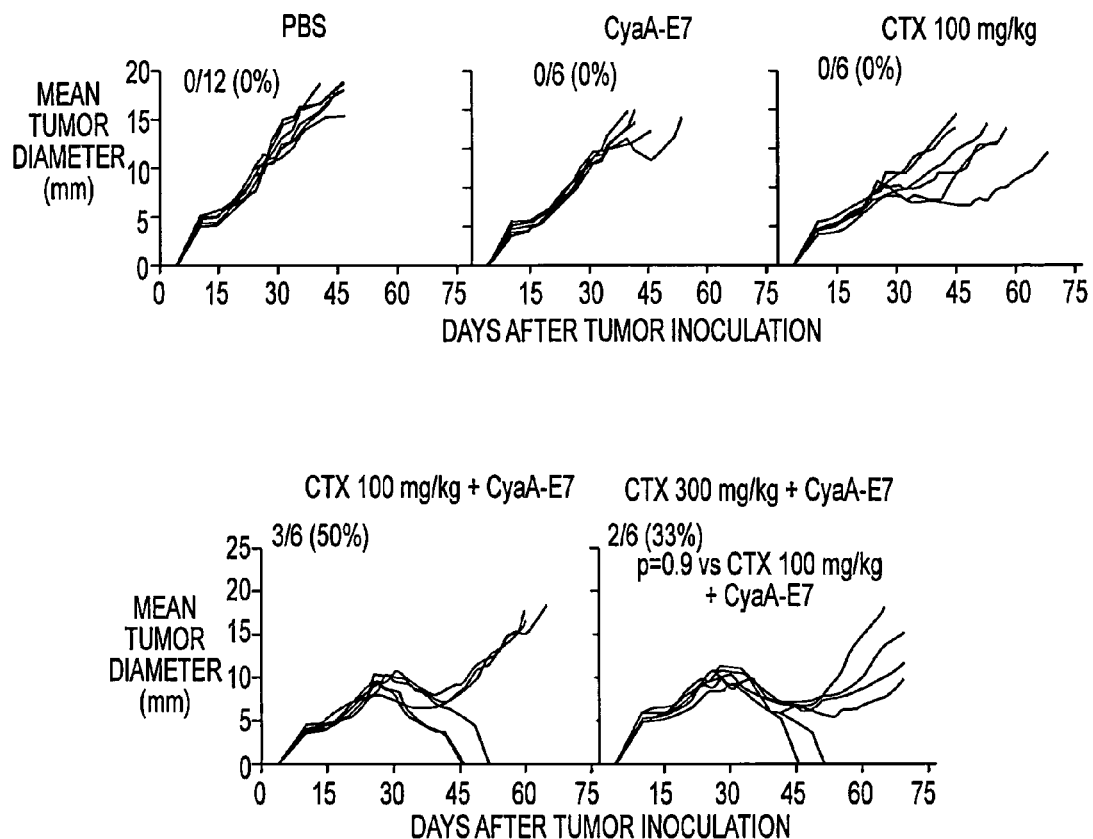
FIG. 2.2A
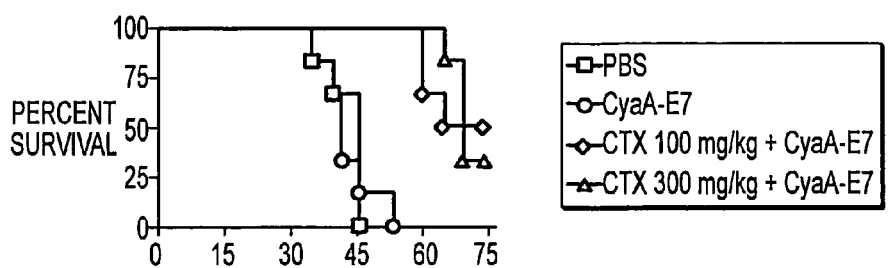
FIG. 2.2B

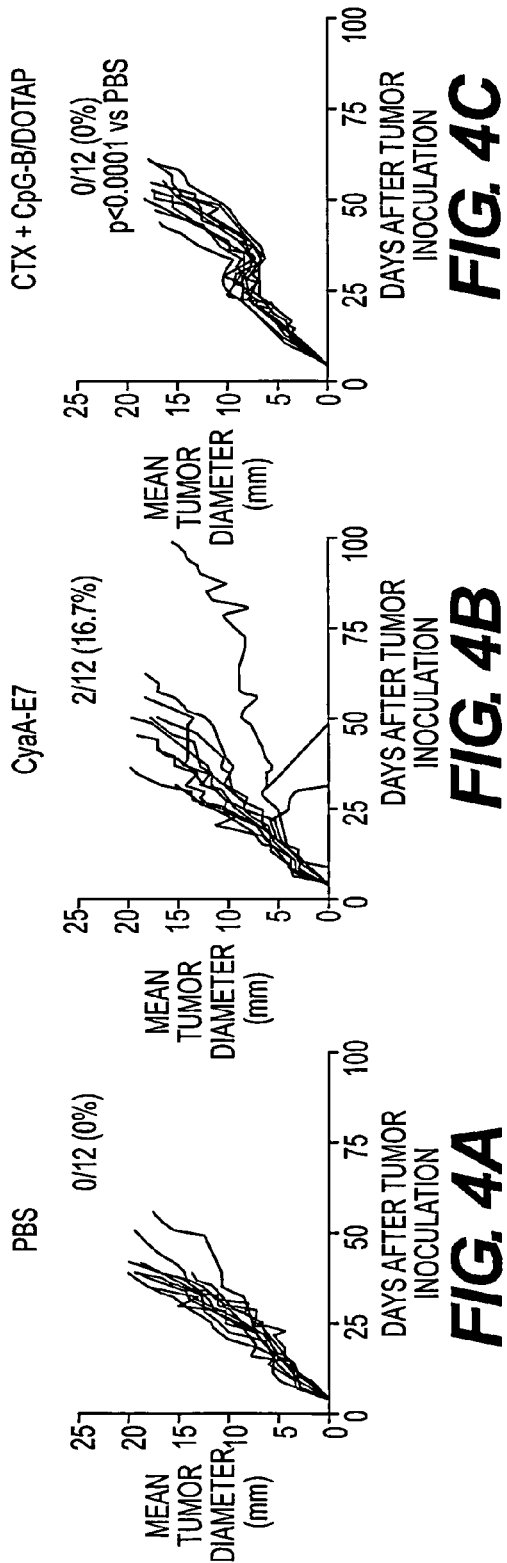

FIG. 5.1A
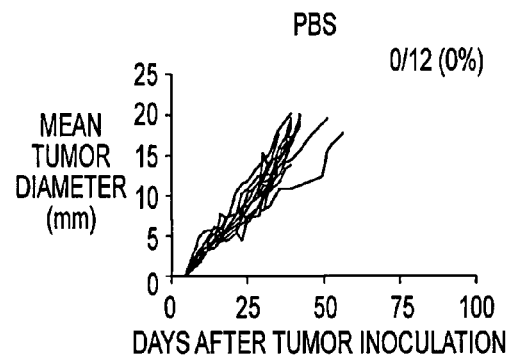
FIG. 5.1B
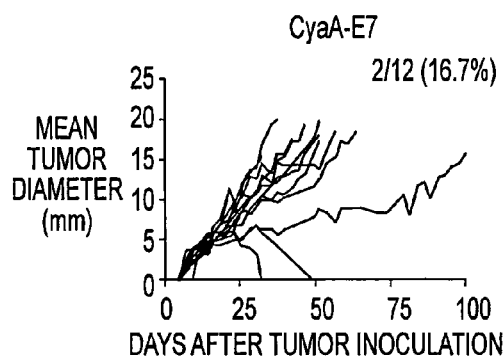
FIG. 5.1C
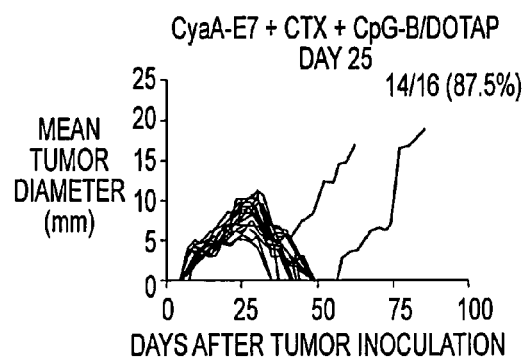

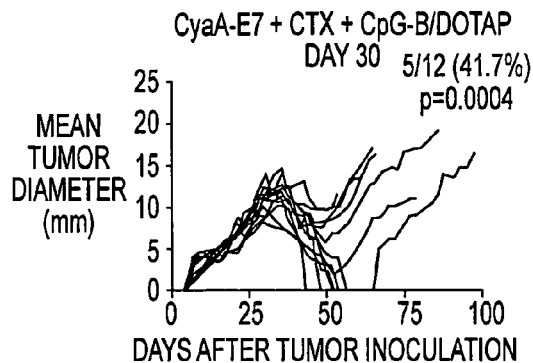
FIG. 5.1D
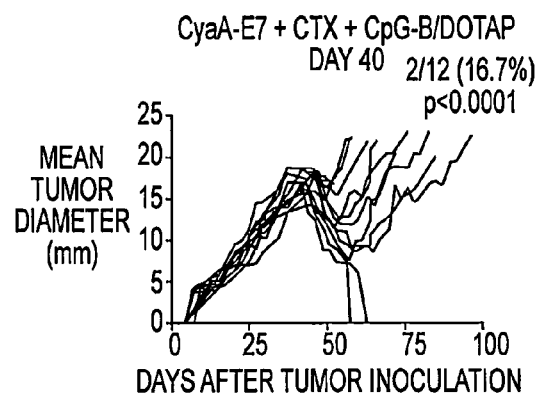
FIG. 5.1E
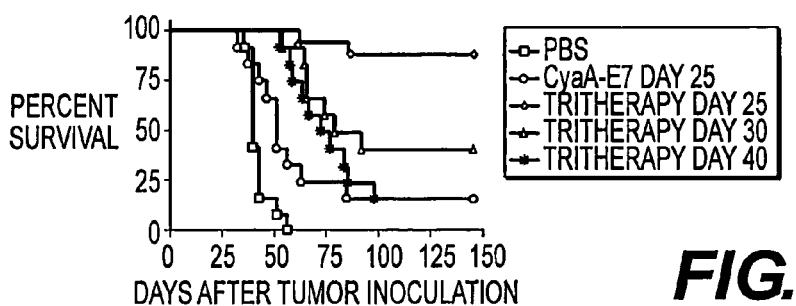
FIG. 5.1F

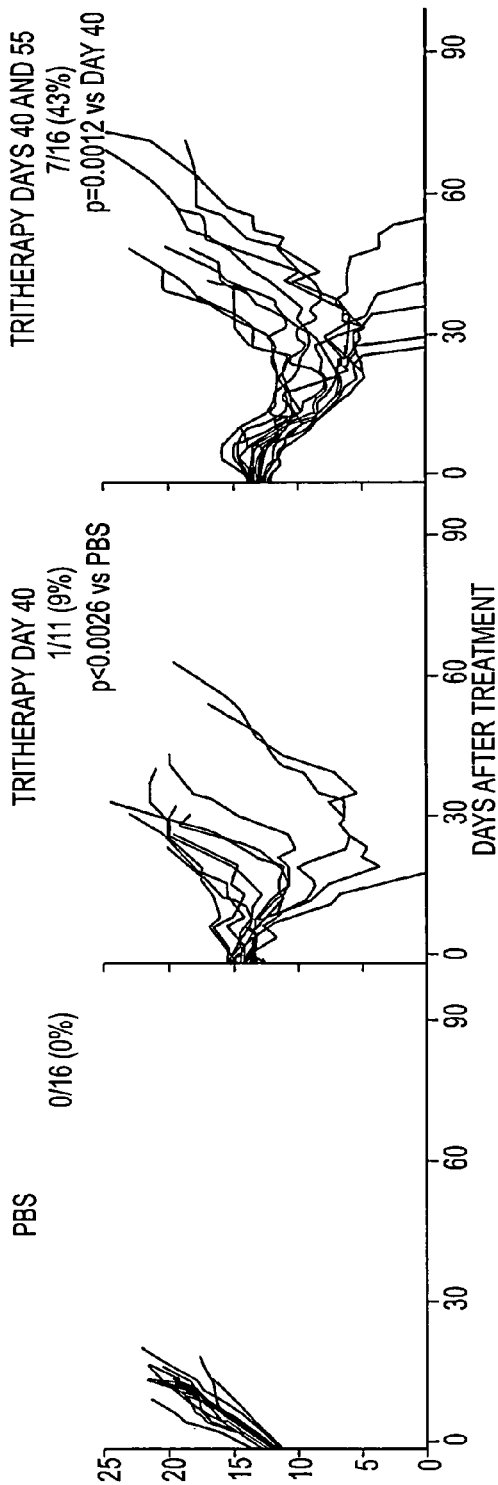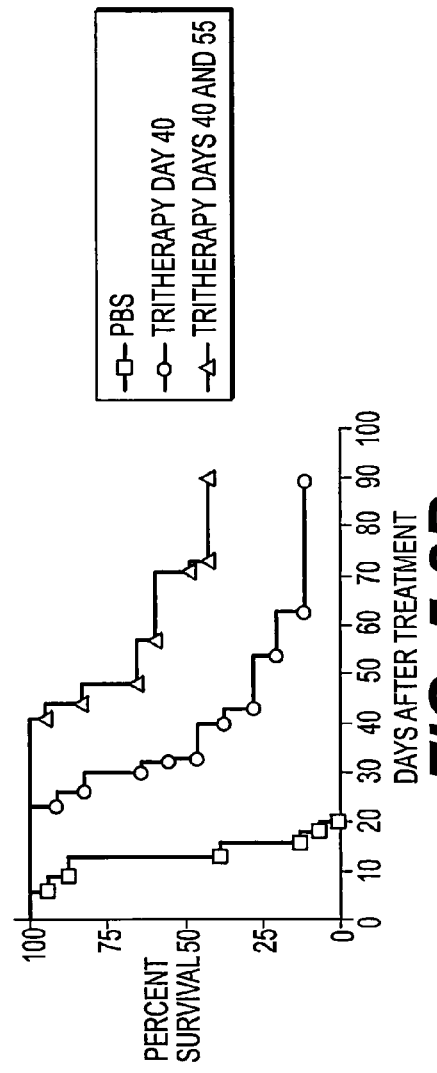
FIG. 5.2A
FIG. 5.2B

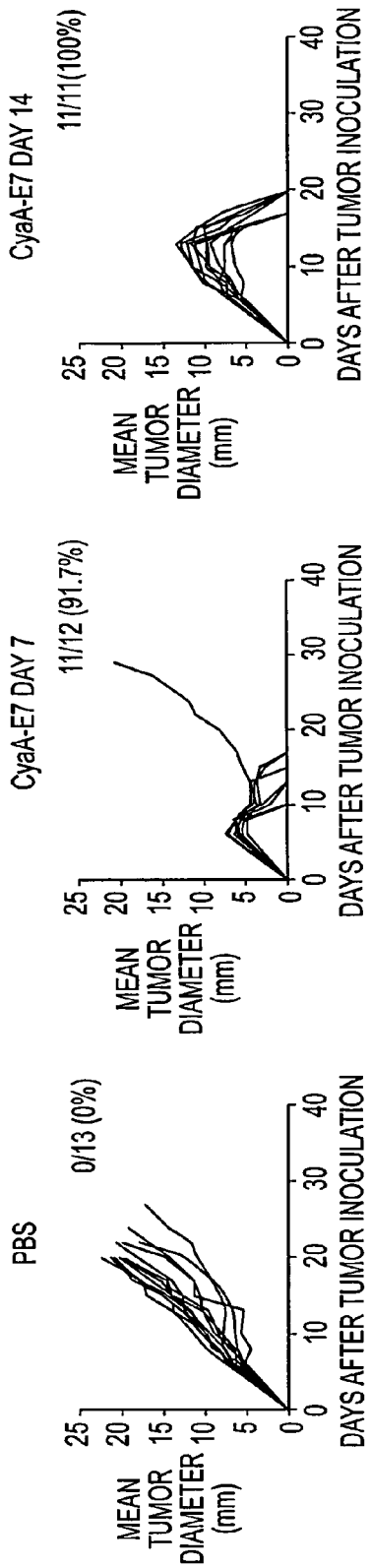

Figure 7A:
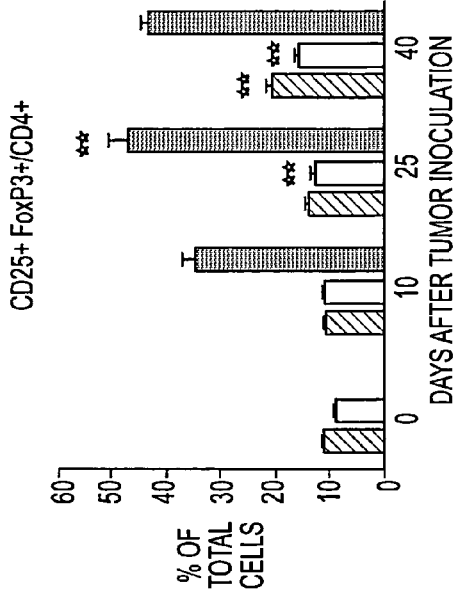

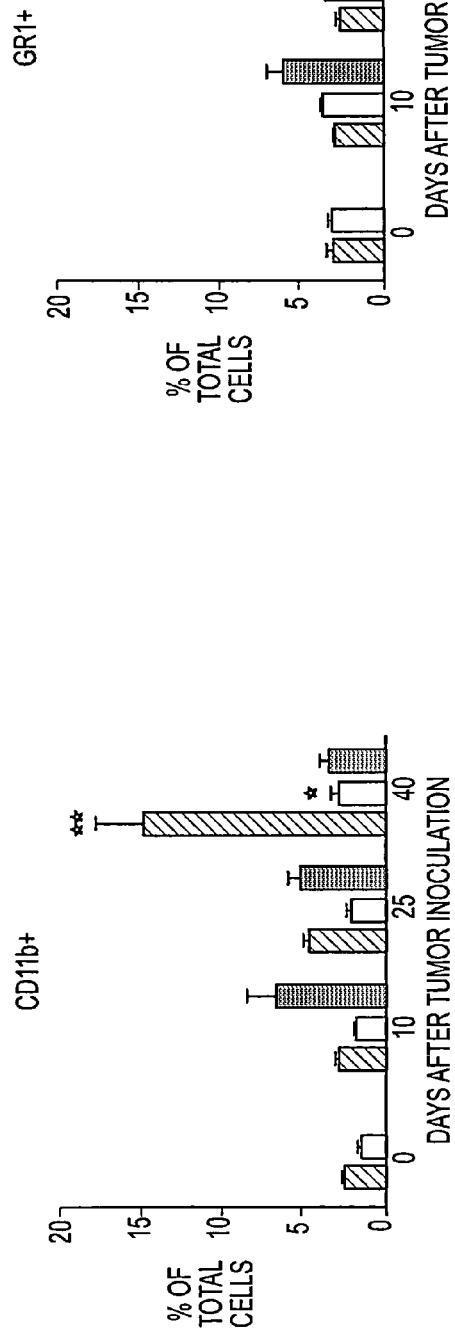
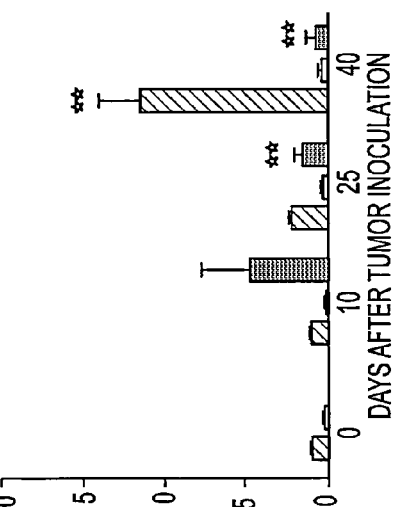
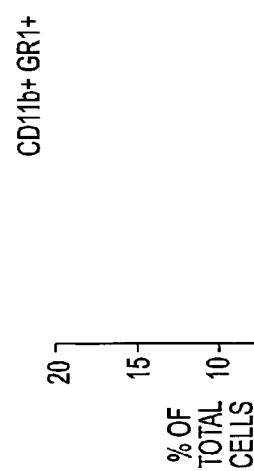
FIG. 7D
FIG. 7E
FIG. 7F

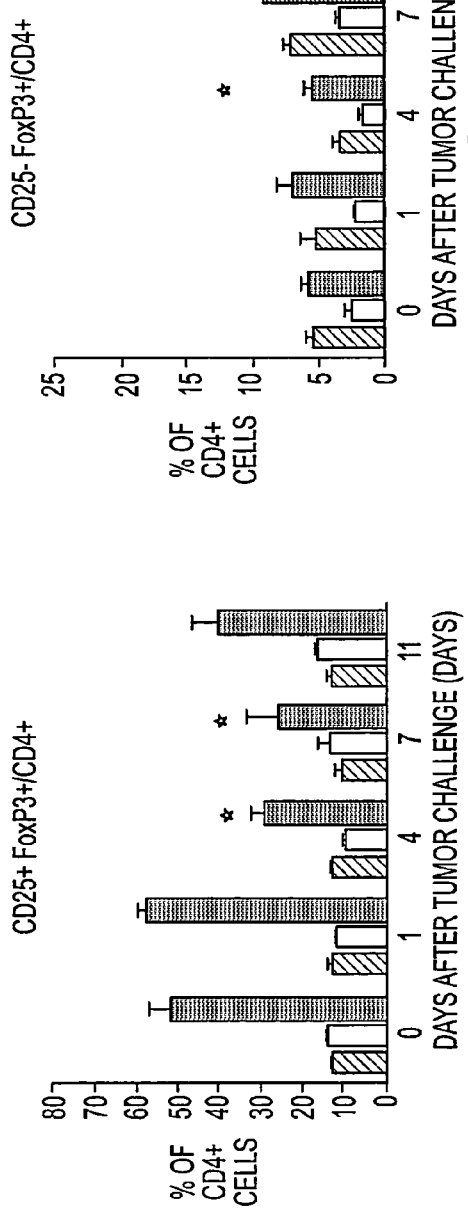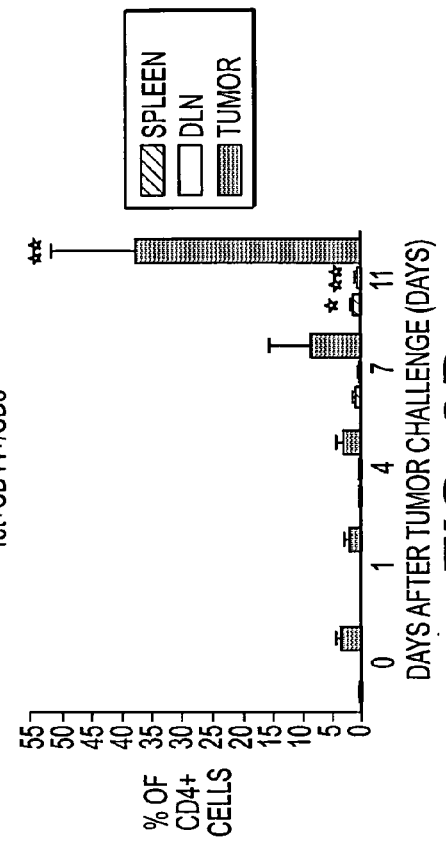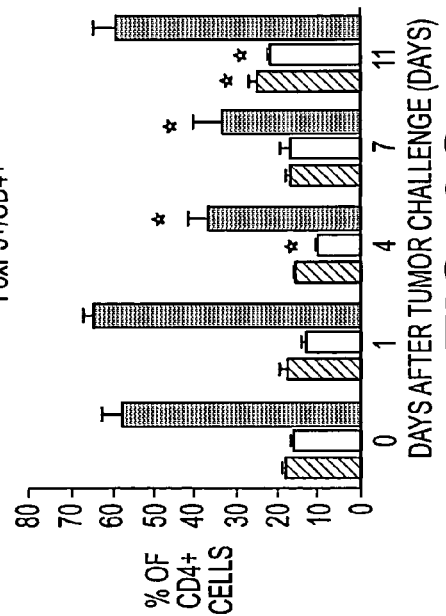

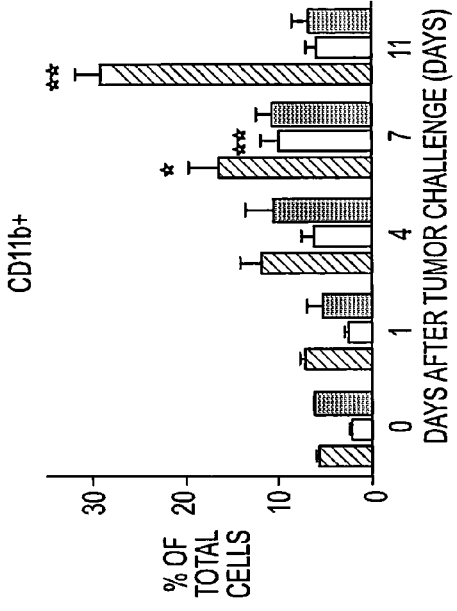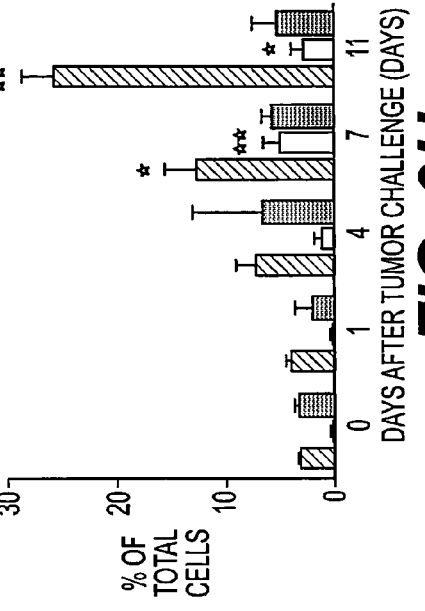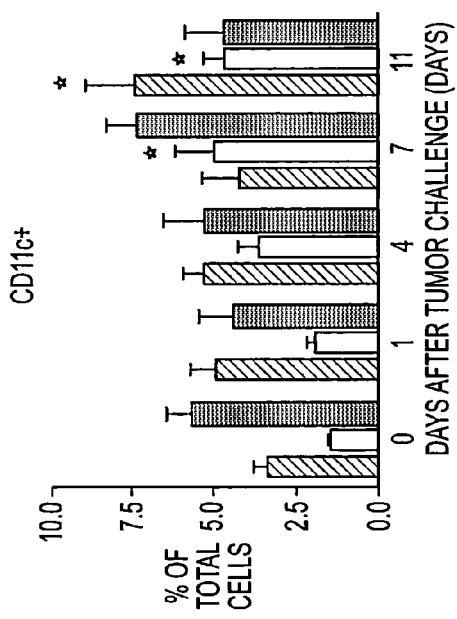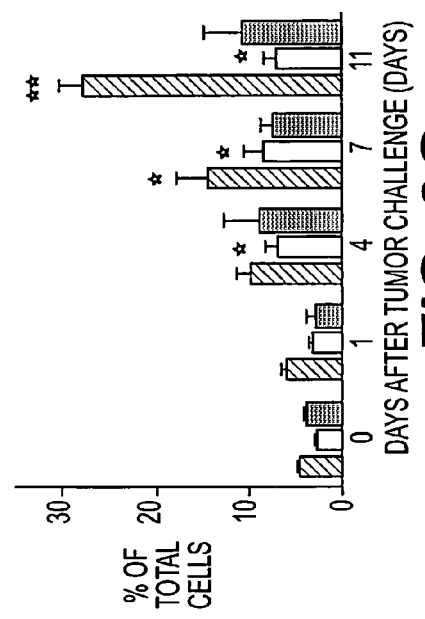

SEQUENCE LISTING

<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala His Tyr Asn Ile Val Thr Phe
1               5

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 3
<211> LENGTH: 9
<212> TYPE: PRT
<213> ORGANISM: Human papillomavirus

<400> SEQUENCE: 3

Ile Asp Gly Val Asn His Gln His Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ile or Ala
<220> FEATURE:
<221> NAME/KEY: MOD_RES
<222> LOCATION: (2)
<223> OTHER INFORMATION: Asp or Ser

<400> SEQUENCE: 4

Xaa Xaa Gly Val Asn His Gln His Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ser Gly Val Asn His Gln His Leu
1               5

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gggggacgat cgtcggggggg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tccatgacgt tcctgacgtt                                               20

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctagccgtgc ccattacaat attgtaacct ttggtac                            37

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caaaggttac aatattgtaa tgggcacgg                                     29

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggcgctagc atgcatggag atacacctac                                    30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

-continued gggcggtacc tggtttctga aacagatgg g                                    31

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggcaccggt aaacgtatgc acggcgatac tccg                                34

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgtgagcatc tggctttcac tagtacgttt gttcagctgc tcgtagca                 48

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggcactagt gaaagccaga tgctcacgcg cggg                                34

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agtacatccg gcgagaac                                                  18

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gggcgctagc ggtcaagcag aaccggac                                       28

<210> SEQ ID NO 17
<211> LENGTH: 56
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 17
gggcggtacc aggtttttga gagcaaatcg gacaaacaat ccccagagta cccatc        56
```

THERAPY OF CANCER BASED ON TARGETING ADAPTIVE, INNATE AND/OR REGULATORY COMPONENT OF THE IMMUNE RESPONSE

This application claims the benefit of U.S. Provisional Application No. 60/879,333, filed Jan. 9, 2007, which claims the benefit of EP 06291393.4, filed Sep. 1, 2006, all of which are incorporated herein by reference.

The invention relates to components suitable for the design of a therapy of cancer based on targeting adaptive, innate and/or regulatory component of the immune response in a patient.

The invention especially relates to the association, in a kit of parts, of compounds suitable for targeting the immune system in a human patient by eliciting the adaptive and either or both of innate and regulatory components of the immune response.

The invention therefore concerns the use of compounds associated in a kit of parts for the treatment of patients in need thereof, especially for the treatment of patients suffering from a malignant tumor or from a cancer or for preventing the onset or the maintenance of the malignant transformation of a tumor.

In particular, the invention relates to the field of viral induced cancer, especially of cancer induced following papillomavirus infection of a host.

Successful implementation of the immunotherapeutic approaches developed in murine tumor models for human malignancies remains a major challenge, despite the intense efforts to improve the two main components of classical vaccines, i.e., the antigen delivery system and the adjuvant. In order to target antigen to the dendritic cells (DCs), the inventors have developed a new delivery system based on the adenylate cyclase (CyaA) of *Bordetella pertussis*. CyaA binds specifically to the $\alpha_M\beta_2$ integrin (CD11b/CD18) (1) and delivers its catalytic domain into the cytosol of $CD11b^+$ cells (2). Thus, $CD4^+$ and $CD8^+$ T cell epitopes inserted into the catalytic site of CyaA are processed and respectively presented by MHC class II and I molecules at the surface of DCs (3). The inventors have previously reported the strong therapeutic antitumor immunity induced in mice by a recombinant CyaA carrying the ovalbumin protein against tumors expressing this antigen (4). Recently, a recombinant CyaA carrying a modified form of the E7 protein of the human papillomavirus (HPV) 16 (CyaA-E7) was shown to induce the eradication of palpable tumors generated by the s.c. graft of E6/E7 expressing TC-1 cells, a validated model for testing the efficacy of immunotherapeutics against HPV-associated neoplasia (5) (WO 2005/089792).

Cervical carcinoma is the second most common cancer in women, after breast cancer, worldwide and the fifth most frequent cancer overall, with an estimated prevalence of 1.4 million cases (6). There is now consistent evidence that cervical cancer is due to the chronic infection of the genital tract by some mucosatropic types of HPV (7). The expression of HPV oncogenic proteins E6 and E7 is required for the onset (8) and the maintenance of malignant transformation (9). Interestingly, cellular immunity to E7 was found to be associated with clinical and cytologic resolution of HPV-induced lesions (10). These findings make HPV-neoplasia valuable candidates for the development of immunotherapeutic strategies.

The inventors have now envisaged how improvement of the anti-cancer vaccines currently available could be realized. They have made the hypothesis that such an improvement could be achieved through the stimulation of innate immunity, in particular through toll-like receptors (TLRs), the natural sensors for infection. Although members of the TLR family all share certain structural and functional properties, the signals delivered by various TLRs may elicit qualitatively and quantitatively different immune responses (11). Another different envisaged approach is the combination of vaccine candidates eliciting adaptive immune responses, with chemotherapeutic compounds. Chemotherapy can help to enhance antitumor immunity by reducing the tumor burden, by increasing the CTL sensitivity of tumor cells (12) or by killing/inactivating immune regulatory cells (13).

In the present invention, the inventors designed different treatment regimens and compared their capacity to enhance the antitumor immunity induced by CyaA recombined with a tumor-associated antigen, especially in a tumor setting where this vaccine is not able to control the growth of large, established tumors.

The invention provides a kit of parts of compounds suitable for use in an anticancer therapy, wherein said kit of parts comprises:

(i) a recombinant protein comprising one or several polypeptides bearing one or several epitopes of one or several tumor-associated antigens, said polypeptides being inserted in the same or different permissive sites of an adenylate cyclase (CyaA) protein or of a fragment thereof, wherein said CyaA fragment retains the property of said adenylate cyclase protein to target Antigen Presenting Cells or a mixture of such recombinant proteins wherein at least one of said epitopes, or tumor associated antigens, or insertion sites of CyaA protein, or fragment of said CyaA protein is different between the various recombinant proteins in the mixture; and said kit of parts further comprises (ii) an agent, suitable for modulating a regulatory cell response in a patient.

In a particular embodiment of the invention, a regulatory cell response which is modulated encompasses modulating a Lymphoid suppressor cells response, especially a regulatory T cell response, induced by tumor (including tumor microenvironment).

In a particular embodiment the regulatory cell response which is modulated encompasses modulating a Myeloid suppressor cells (MSC) response induced by tumor (including tumor microenvironment).

In a particular embodiment of the invention, the kit of parts comprises each of the following compounds: (i), a recombinant protein comprising one or several polypeptides bearing one or several epitopes of one or several tumor-associated antigens, said polypeptides being inserted in the same or different permissive sites of an adenylate cyclase (CyaA) protein or of a fragment thereof, wherein said CyaA fragment retains the property of said adenylate cyclase protein to target Antigen Presenting Cells or a mixture of such recombinant proteins wherein at least one of said epitopes, or tumor associated antigens, or insertion sites of CyaA protein, or fragment of said CyaA protein is different between the various recombinant proteins in the mixture; and said kit of parts further comprises at least one of the following compounds;

(ii) an agent, suitable for modulating the regulatory cell response in a patient and, (iii) an adjuvant component suitable for activating innate immune response(s) in a patient.

In another particular embodiment of the invention, the active principles of the kit of parts consist of each of compounds (I), (ii) and (iii).

The expression "kit of parts" relates to the association, in the treatment regimen intended for a patient in need thereof, of at least two of the different compounds defined above and disclosed herein, in order to provide a therapeutic effect that would not be obtained identically by the administration of one of these compounds when used alone in a patient in need thereof. Said association requires the use, either separated or simultaneously in time, of the at least two compounds defined in the present invention which compounds are presented separately. The association according to the invention of the compounds defined in the present application provides a novel effect resulting from their use in a combined therapy.

According to the invention, therapy is especially intended for mammalian hosts, i.e., patients, including especially human being but also animals.

In a particular embodiment of the invention, the kit of parts comprises 2 or more recombinant CyaA proteins as defined herein.

The invention also relates to a composition comprising (i) a recombinant protein comprising one or several polypeptides bearing one or several epitopes of one or several tumor-associated antigens, said polypeptides being inserted in the same or different permissive sites of an adenylate cyclase (CyaA) protein or of a fragment thereof, wherein said CyaA fragment retains the property of said adenylate cyclase protein to target Antigen Presenting Cells or a mixture of such recombinant proteins wherein at least one of said epitopes, or tumor associated antigens, or insertion sites of CyaA protein, or fragment of said CyaA protein is different between the various recombinant proteins in the mixture and, (ii) an agent, suitable for modulating a regulatory cell response in a patient.

The composition may also comprise (iii) an adjuvant component suitable for activating innate immune response(s) in a patient.

In the composition, the components are preferably in a mixture.

The invention also concerns a kit of parts comprising compounds (i), (ii) and (iii) as defined above, wherein two of these compounds are associated in a composition and the third compound is presented separately.

A particular kit of parts according to the invention comprises a composition containing a recombinant protein comprising one or several polypeptides bearing one or several epitopes of one or several tumor-associated antigens, said polypeptides being inserted in the same or different permissive sites of an adenylate cyclase (CyaA) protein or of a fragment thereof, wherein said CyaA fragment retains the property of said adenylate cyclase protein to target Antigen Presenting Cells or a mixture of such recombinant proteins wherein at least one of said epitopes, or tumor associated antigens, or insertion sites of CyaA protein, or fragment of said CyaA protein is different between the various recombinant proteins in the mixture and an adjuvant component suitable for activating innate immune response(s) in a patient and, as a separate compound, an agent suitable for modulating a regulatory cell response in a patient.

The ability of the compounds of the kit of parts or of the composition to activate innate immune responses can be first assayed having recourse to screening, especially functional screening in vitro.

Accordingly, activation of innate immune response can be tested on cells in vitro, such as dendritic cells, since it is acknowledged that immune potentiators or adjuvants stimulate immune cells in vitro thereby enabling the measurement of induced cytokines and/or chemokines produced, either by immune cells or by primary cells including human peripheral blood mononuclear cells. Measurement can be carried out by performing assays such as an ELISA assay. Other tests for measurement of the activity of putative or known potentiators of the innate immune response, in order to determine their ability to act as adjuvant component according to the invention are disclosed in the examples.

Activation of the adaptive immune response dependant on the functional activity of the recombinant CyaA proteins described herewith can be tested as shown in the examples, especially by measuring the cytotoxic activity of T cells by tetramer or in vivo lysis or by measuring tumor growth, especially on animals (especially mammalian) inoculated with tumor cells, after treatment with said recombinant CyaA protein(s). Tumor growth can be determined in comparison with models as disclosed in the examples hereafter.

An agent suitable for modulating a regulatory cell response, especially a T cell regulatory cell response or a MSC response is in particular suitable to achieve depletion of a regulatory immune cells, or to functionally inactivate the regulatory immune cells, or to reverse the regulatory immune cell response that induces detrimental immunosuppressive effect in the tumor-bearing host. It may also or alternatively inhibit the production or activity of products of said regulatory immune cells.

Alteration of regulatory immune response, especially of tumor-induced regulatory T cell response, can be assayed through various tests, in vivo or in vitro, including those performed in the examples disclosed hereafter. Appropriate tests can also be performed in vitro, Regulatory T cells encompass a subgroup of $CD4^+$ cells ($T_{reg}$ cells) or of $CD8^+$ cells ($CD8^+$ regulatory T cells) in humans and $CD4^+$ cells in mice. Reference is especially made to Zou et al (Nature Reviews/Immunology, vol 6, April 2006, p 265-305) for the description of assays. Especially, activity of regulatory T cells on APC (Antigen Presentation Cell) can be tested in vitro, especially having recourse to the detection of induction of B7-H4 expression by APC which is normally enabled by regulatory T cells, or alternatively having recourse to the detection of killing of T cells or APCs. In vivo test for activity of regulatory T cells, and accordingly the effect of selected compounds on this activity, can be carried out by measuring the release of interleukin-10 (IL-10) and transforming growth factor (TGF beta), since regulatory T cells release these factors in vivo, or by inhibition of expression of MHC molecules such as CD80, CD86 and IL-12 which results in the inhibition of the T cell activity or APC function when regulatory T cells activity is not suppressed.

It has been observed by the inventors that an agent suitable for depleting a regulatory cell response, especially a T cell response or a MSC response, may be active with respect to the immune compartment of subjects carrying a tumor of a stage corresponding to infiltrating or vascularized tumors or metastatic tumors, more efficiently than it might act on superficial or non-established tumors.

Treg cells expansion observed in hosts presenting tumors may be detected in the tumor itself or/and, for some of them, in other compartments such as spleen or lymph nodes.

Examples of Treg cells are CD4+ regulatory T-cells and especially $CD4^+CD25^+$Treg cells or CD4+ $CD25^-$ Treg cells. More particular examples of Treg cells are $CD4^+CD25^+$Fox $P3^+$ cells or $CD4^+CD25^-$FOxP3$^+$ Treg cells. It has also been observed that regulatory T cells in human may be a subset of $CD8^+$ Treg cells such as $CD8^+$ $CD25^+$ Treg cells or $CD8^+$ $CD25^-$T cells or $CD8^+$ IL10$^+$ T cells. The $CD4^+$ Treg cells may be naturally occurring Treg cells or adaptively induced Treg cells.

Another Example of Treg Cells Includes NKT Regulatory Cells

According to another embodiment the agent suitable for modulating the regulatory cell response modulates the activity of other categories of cells also having a suppressive activity and accordingly the agent enables inactivation or modulation such as maturation towards a non suppressive phenotype. Such categories of cells encompass myeloid suppressive cells which derive from hematopoietic cells and accumulate in subjects confronted with tumors. For illustration, a myeloid derived CD11b$^+$GR1$^+$ cell population has been found to increase in subjects affected with tumors as described herein.

The compounds of the kit of parts of the invention or of the composition can be formulated to facilitate their uptake and especially can be formulated with pharmaceutically acceptable vehicles, carriers or appropriate delivery systems available for vaccines, such as liposomes, oil-in-water emulsions, surface active agents, microparticles.

The above defined CyaA protein especially carries CD4$^+$ and/or CD8$^+$ T cell epitopes of one or several antigens present on a tumor, that may be inserted into permissive sites of said protein, especially inserted into the catalytic site of CyaA. As a result, when administered to a patient, the CD4$^+$ or CD8$^+$ epitopes are processed and respectively presented by MHC class II and I molecules at the surface of Dendritic Cells (DCs) thereby enabling stimulation of the immune, adaptive, response in a patient.

In a particular embodiment, the CyaA protein including full-length CyaA or its fragment (said "fragment" comprising more than 2 amino acid residues) also retains the property of CyaA to allow translocation of the epitope(s) inserted therein or of the polypeptide(s) containing said epitope(s) into the cytosol of a target cell. Translocation of the epitope(s) or polypeptide(s) containing said epitope(s) into the cytosol of the target cell can be permitted if the fragment of CyaA retains the domain of the protein which permits translocation of its catalytic domain.

In a particular embodiment, the polypeptide(s) is inserted at a location in CyaA or a fragment, corresponding to the position between codons 224 and 225.

The recombinant protein of the invention can be prepared having recourse to recombinant technology. It can also be obtained by synthesis, especially by chemical synthesis. Hence, the terms "recombinant protein" refers to the chimeric form of the protein.

The capacity of the recombinant protein to target CD11b/CD18 cells can be assayed especially according to the methods disclosed in EP 03291486.3 and El-Azami-El-Idrissi M. et al, J. Biol. Chem., 278(40)38514-21 or in WO 02/22169. Furthermore, the capacity of the recombinant protein to translocate the epitope(s) or polypeptide(s) containing said epitope(s) into the cytosol of target cell can be assayed by applying the method described in WO 02/22169.

In a particular embodiment, the fragment of CyaA used in the recombinant protein can be constituted of two different portions of CyaA which are not naturally contiguous in CyaA. As an example, one may cite the catalytic domain of CyaA, i.e., the 400 amino acid residues of the N-terminal part of CyaA and a fragment comprising amino acid residues 1208 to 1243 required for targeting of CD11b/CD18 Antigen Presenting Cells.

In the above definition, the expression "polypeptide" describes any molecule having an amino acid sequence, including amino sequences undergoing post-translational modifications, especially an amino acid sequence having at least six amino acid residues, and including amino-acid sequences having especially from 5 to 500 residues or from about 5 to about 100, or from about 5 to about 200 or from about 10 to about 50 residues, or from about 30 or about 50 to 200 residues, or from about 100 to about 250 (or especially 210) or from about 100 to about 200 residues providing said amino acid sequence comprises at least one epitope, i.e., an amino acid sequence against which an immune response may be obtained after its delivery to a target cell, advantageously in a host, especially in a mammal, in particular a human host. Polypeptides according to this definition can thus be restricted to epitopes, even to a unique epitope or can comprise several different or identical epitopes or can also encompass full-length antigens from a pathogen, i.e., from human papillomavirus or tumor-associated antigens or epitopes thereof. Epitopes within the present invention encompass molecules having amino acid sequences which are involved in humoral immune response and/or cell-mediated immune response, especially in T cell immune response. Accordingly, epitopes in the polypeptides of the recombinant molecules of the invention include those which are processed by APC (Antigen Presenting Cells) in a host, especially those recognized in association with class I MHC (Major Histocompatibility Complex) molecules such as epitopes which target cells are CD8$^+$ T lymphocytes or epitopes recognized in association with class II MHC molecules such as those which target cells are CD4$^+$ T lymphocytes cells.

According to the invention, adenylate cyclase (CyaA) is used as a full-length protein or as a fragment thereof, as disclosed above.

Advantageously, the CyaA protein or a fragment thereof is a protein or a fragment thereof, wherein the protein is the result of the co-expression in a cell, especially in a recombinant cell, of both cyaA and cyaC genes. It has been indeed shown that in order to have invasive properties for target cells, CyaA has to undergo post-translational modifications which are enabled by the expression of both cyaA and cyaC genes (WO 93/21324).

In a particular embodiment of the invention, fragments of the CyaA protein are fragments having at least about 30 amino acid residues and can have up to about 1300, in particular to about 500 amino acid residues, preferably from about 50 to about 150 amino acid residues; said fragments comprise, in a particular embodiment, amino acid residues from about 1166 to about 1281 of CyaA or amino acid residues 1208 to 1243 of CyaA protein for interaction with CD11b/CD18 target cells. A particular fragment thus encompasses all or part of the C-terminal part of the native protein which part is responsible for the binding of the protein to target cell membrane and/or CD11b/CD18 receptor, and for the subsequent delivery of the epitope(s) contained in the polypeptide(s) into the cell cytosol (Ladant D. et al., Trends Microbiol., 7:172-176, 1999). A particular fragment of CyaA protein according to the invention contains amino acid residues 372 or 373 to 1706 of CyaA protein. Another particular fragment is one which corresponds to the CyaA protein wherein amino acid residues 225 to 234 have been deleted, thus providing a CyaA fragment containing residues 1 to 224 and 235 to 1706.

In a particular embodiment of the invention, the adenylate cyclase protein is a bacterial protein. In a preferred embodiment, CyaA protein is derived from a *Bordetella* species. By the expression "derived from a *Bordetella* species", it is meant that the protein reflects the protein produced by said *Bordetella* species. It can however be recovered, produced or expressed by any available techniques.

Among *Bordetella* species of interest, according to the invention, one of them is *Bordetella pertussis*. Other *Bordetella* strains of interest are those of *Bordetella parapertussis* or *Bordetella bronchiseptica*. The sequences of CyaA protein of *B. parapertussis* has been disclosed especially under accession number NC 002928.3 (as a sequence of 1740 amino acids) and in Parkhill J. et al (Nat. Genet. DOI, 10 (2003) and for *B. bronchiseptica* in Betsou F. et al (Gene 1995, August 30; 162(1): 165-6).

The adenylate cyclase toxin (CyaA) is a critical virulence factor of the bacterium and is one of the antigens protective against *B. pertussis* infection.

The adenylate cyclase protein of *Bordetella pertussis* is a toxin which has been described as a bifunctional protein of 1706 residues, comprising a N-terminal catalytic domain of 400 amino acid residues and a C-terminal part of 1306 residues which is responsible for the binding of the toxin to target cell membrane and subsequent delivery of the catalytic moiety into the cell cytosol (Ladant et al, 1999).

The CyaA protein is synthesized as an inactive protoxin which is converted into an active toxin by post translational palmitoylation of two internal lysine residues (lysins 860 and 983). This post translational modification requires the expression with the cyaA gene of an accessory gene, i.e., cyac which is located nearby cyaA on *B. pertussis* chromosome.

The cyaA of *Bordetella pertussis* has been described as an amino acid sequence and a nucleotide sequence by Glaser, P. et al (1988 Molecular Microbiology 2(1), 19-30). Accordingly, when amino acid residues or sequences or nucleotides or nucleotide sequences of the CyaA protein of *B. pertussis* are cited in the present invention their positions are given with respect to the sequences disclosed in said publication of Glaser et al. 1988.

For the present invention, a "permissive site" is a site of the sequence of the CyaA protein where a polypeptide can be inserted without substantially affecting the functional properties of the CyaA protein especially without substantially affecting the targeting of cells, particularly targeting of APC by CyaA, including without substantially affecting the specific binding to the CD11b-CD18 receptor and advantageously without substantially affecting the domains of the protein involved in the process of translocation of the epitope(s) into a target cell.

Permissive sites of the *Bordetella pertussis* adenylate cyclase allowing translocation of CyaA catalytic domain and hence translocation of epitopes inserted into such permissive sites include, but are not limited to, residues 137-138 (Val-Ala), residues 224-225 (Arg-Ala), residues 228-229 (Glu-Ala), residues 235-236 (Arg-Glu), and residues 317-318 (Ser-Ala) (Sebo et al., 1995, Infection and Immunity, pages 3851-3857). The following additional permissive sites are also included in embodiments of the invention: residues 107-108 (Gly-His), residues 132-133 (Met-Ala), residues 232-233 (Gly-Leu), and 335-336 (Gly-Gln) and 336-337. (Glaser P. et al, 1988)

For other *Bordetella* species corresponding permissive sites can be defined by comparison of sequences and determination of corresponding residues.

According to another embodiment, the polypeptide can also or alternatively be inserted at one and/or other extremities of CyaA protein or its fragment.

Particular fragments of CyaA proteins for use for the purpose of the invention are those comprising up to 1300 amino acids or from about 30 to about 500 amino acid residues, advantageously about 50 to about 150 amino acid residues in particular such fragments encompassing amino acid residues from about 1166 to about 1281 of the native CyaA protein, advantageously 1208 to 1243 of native CyaA protein.

Thus, according to the invention, the "insertion" of a polypeptide in the CyaA protein including full-length CyaA or fragment thereof to provide a so-called recombinant protein also referred to as a "hybrid protein", encompasses genetic insertion especially by available DNA technology.

Alternatively, "insertion" also encompasses non genetic insertion, including chemical insertion for instance covalent coupling carried out at one extremity of the CyaA or fragment thereof, or non covalent coupling. Non-genetic insertion can especially be of interest when the polypeptide to be inserted is synthetic or semi-synthetic. Methods for coupling a drug to a polypeptide are well known in the Art and comprise for example disulfide linkage by using N-pyridyl sulfonyl-activated sulfhydryl.

In particular, it is possible to graft molecules especially comprising polypeptides of the invention to CyaA by a chemical linkage or by genetic insertion for in vivo targeting to target cells of Cya, such as ACP, for example CD11b/CD18 cells and particularly to the cytosol of said cells. Indeed, when coupling a molecule corresponding to a given CD8+ T-cell epitope to the catalytic domain of detoxified CyaA, either by means of a disulfide bond or by genetic insertion, it has been found that the engineered molecule can elicit in vivo specific CTL response, thereby showing that said CD8+ T-cell epitope is translocated into the cytosol of CD11b-expressing cells.

In a specific embodiment, the recombinant adenylcyclase used for the manufacturing of proteinaceous vector is a CyaA or fragment thereof especially modified by insertion of cysteine residues containing one or more molecule(s), especially comprising polypeptides of the invention, chemically coupled by means of a disulfide bond to genetically inserted cysteine residue(s) located within the catalytic domain of said adenylcyclase.

Indeed, multiple molecules especially comprising polypeptides of the invention, can be chemically coupled to the adenylcyclase by means of a disulfide bond to different cysteine residues located at different permissive sites within the catalytic domain.

According to another particular embodiment of the invention, the polypeptides bearing epitopes have been modified with respect to their native amino acid sequence, for example in order to decrease the number of negatively charged amino acid residues within the sequence. Such a modification can be obtained by removing some of these negatively charged amino acid residues or also by adding some positively charged amino acid residues, especially as flanking residues of the epitopes. Polypeptides thus comprising less negatively charged residues might favour the translocation of the catalytic domain of CyaA protein in the cytosol of target cells.

The polypeptides bearing epitopes can also be designed in such a way that they are unfolded when they are inserted in CyaA or in a fragment thereof, which improve efficiency of the internalization of the polypeptides into the target cells. Such unfolding in polypeptides which undergo folding as a consequence of their amino acid content, can be obtained for instance by removing or substituting cystein residues in order to avoid formation of disulfide bonds that may be involved in folding of polypeptides. In some cases, it is possible to prevent folding of the polypeptides by preparing them in the presence of reducing agents to enable avoiding in vivo refolding.

In a particular embodiment, the epitopes borne by the polypeptides can be cryptic epitopes.

In a particular aspect of the invention, the inventors have indeed determined that the chimeric protein constructs, made of the recombinant proteins which comprise (a) an adenylate cyclase (CyaA) or a fragment thereof according to the definitions disclosed herein and (b) a polypeptide bearing one or several antigenic fragments of one or several antigens, enable cryptic epitopes of said antigens to become immunogenic as a result of their presentation in the recombinant construct. Especially, said chimeric constructs involving CyaA or a fragment thereof as defined in the present invention and polypeptides derived from antigens of interest for especially therapeutic, including vaccinating, purposes can comprise cryptic epitopes of the antigen which are allowed to become immunogenic and in particular to raise a T-cell response in a host, especially a CTL response.

The invention thus also relates to the use, in the kit of parts or composition defined herein, of a recombinant protein comprising one or several polypeptides bearing one or several epitopes of one or several antigens, said polypeptide(s) being inserted in the same or in different permissive sites of an adenylate cyclase (CyaA) protein or of a fragment thereof, said CyaA fragment retaining the property of said adenylate cyclase protein to target Antigen Presenting Cells, wherein at least one of said epitope(s) is a subdominant cryptic T-cell epitope and wherein said recombinant protein is capable of eliciting an antigen-specific response against said polypeptide(s).

In a particular embodiment, in order to prepare the recombinant protein of the kit of parts or composition of the invention, the enzymatic activity of the CyaA protein, i.e., its ability to convert ATP into cAMP, i.e., its catalytic activity, has been inactivated. Accordingly, the recombinant protein used in the kit of parts is detoxified. Such inactivation of the catalytic activity may be obtained as a result of genetic inactivation. As an example, genetic inactivation can be obtained as a result of introduction of a dipeptide in a site of the amino acid sequence of CyaA which is part of the catalytic site (for example between residues 188 and 189). Such an inactivated CyaA protein is illustrated in Preville et al (Cancer Res 2005; 65: 641-9) and in the example below describing its production.

The recombinant protein of the invention is advantageously capable of eliciting a cell-mediated immune response. It includes CTL and Th, especially Th1 response, including CD4$^+$ T cell response and/or CD8$^+$ T cell response.

The ability of the recombinant protein to elicit this cell-mediated immune response has especially been shown to be sufficient to prevent tumor growth in vivo or even to enable tumor regression in an animal. It has also now been shown to be enhanced by activation of innate component of the immune response through TLR activation and by down activating the regulatory component of the immune response through the use of chemotherapeutic agents.

In a particular embodiment of the invention, the tumor-associated antigen is an antigen of papillomavirus (HPV).

In a particular embodiment of the invention, the recombinant protein thus comprises one or several polypeptides bearing one or several epitopes of one or several HPV tumor-associated antigens, that are inserted in one or several permissive sites of the CyaA protein or its fragment.

The recombinant protein of the invention is advantageously capable of eliciting a cell-mediated immune response against HPV associated-tumor. It includes CTL and Th, especially Th1 response, including CD4$^+$ T cell response and/or CD8$^+$ T cell response.

For a recombinant protein suitable for the design of compounds suitable for the kit or parts or composition of the invention and capable of eliciting an immune response, especially a cell-mediated immune response in a host, and in particular in order to design such compounds capable of eliciting an immune response against the malignant effects observed in a host infected with HPV, the inventors have proposed to derive polypeptides bearing epitopes from highly oncogenic HPV strains and especially from antigens from strains selected among HPV16, HPV18, HPV31, HPV33, HPV35, HPV45, HPV52 or HPV58.

Among these strains, HPV 18 and HPV 16 are of particular interest. HPV 16 is especially a particular target for treatment of a host infected with HPV, because of its association with the development of cervical cancer in mammal host especially in human.

Starting from these HPV strains, the inventors propose to derive polypeptides bearing epitopes from antigens selected among L1, L2, E1, E2, E4 and E5 proteins.

Alternatively or in combination, the inventors also propose to derive such polypeptides bearing epitopes from E6 or E7 proteins of HPV.

In a particular embodiment of the invention, E6 or E7 proteins of HPV16 or E6 or E7 proteins from HPV18 are used for the design of polypeptides bearing epitopes.

A particular HPV protein which can be referred to for the design of a polypeptide derived from HPV antigens is the E7 protein of HPV, especially E7 of HPV16 or of HPV18. According to an embodiment of the invention, the polypeptide is derived from several E7 proteins of different HPV strains, especially of HPV16 and HPV18. For example, the polypeptide is the full length E7 protein of HPV 16 and HPV18 or one or several fragments of each of the E7 protein of HPV16 or HPV18, including multimers, especially dimers of said fragments.

These proteins of HPV and their amino acid and nucleotide sequences have been disclosed in Seedorf, K. et al (Human papillomavirus type 16 DNA sequence. Virology, 145: 181-185, 1985) for HPV16, Cole S. T., Danos O. (Nucleotide sequence and comparative analysis of the human papillomavirus type 18 genome. Phylogeny of papillomaviruses and repeated structure of the E6 and E7 gene products. J. Mol. Biol. 193: 599-606 (1987)) or in Fernando G J. et al (T-helper epitopes of the E7 transforming protein of cervical cancer associated human papillomavirus type 18 (HPV18) Virus Res. 1995 April 36(1): 1-13).

The E6 and E7 proteins are oncoproteins expressed especially by HPV16 or HPV18 throughout the replicative cycle of the virus and they have shown to be necessary for the onset and maintenance of malignant transformation of host cells, following infection with HPV strain. Therefore, both these tumors specific antigens are considered as potential targets for adoptive CTL-mediated immunotherapy.

According to a particular embodiment of the invention, the recombinant protein comprises multiple polypeptides, each of them bearing one or several epitopes of one or several HPV antigens.

For example, such multiple polypeptides can be derived from E6 and E7 proteins of one HPV strain, especially from HPV16 or HPV18. According to another example, these multiple polypeptides can encompass epitopes derived from E6 or E7 proteins, from both HPV16 and HPV18.

Multiple polypeptides can also consist of different epitopes bearing fragments of one protein, for example of an E7 or E6 protein, which are inserted in different permissive sites of the CyaA protein of interest.

Another particular recombinant protein according to the above definitions is a recombinant CyaA protein wherein the multiple polypeptides bearing epitopes encompass a fragment comprising residues 1 to 29 or a fragment consisting of residues 1 to 29 or a fragment comprising residues 42 to 98 or a fragment consisting of residues 42 to 98 of E7 protein of HPV16, or multiple polypeptides comprising or consisting of both fragments, inserted in different permissive sites of the CyaA protein.

Another recombinant protein according to the invention is a protein wherein the multiple polypeptides encompass a fragment having amino acid sequence RAHYNIVTF (SEQ ID NO: 1) (E7$_{49-57}$) and/or GQAEPDRAHYNIVTFCCK-CDSTLRLCVQSTHVDIR (SEQ ID NO: 2) (E7$_{43-77}$).

It has been observed that the number of amino acid residues of the polypeptides inserted in permissive sites of the CyaA protein or a fragment thereof is such that it allows for polypeptides consisting of full-length antigens, especially of full-length E6 or E7 proteins of HPV to be inserted in CyaA protein or fragments thereof.

Expression vectors for HPV16 antigens have been designed and have been deposited: They consist in plasmids encoding a recombinant protein according to the invention, i.e., pTRACE5-HPV16E7$_{Full}$ (also designated CyaAE5-HPV16E7$_{FULL}$), deposited at the CNCM (Paris, France) on Mar. 18, 2004 under number CNCM I-3191; pTRACE5-HPV16E7$_{A30-42}$, (also designated CyaAE5-HPV16E7$_{A30-42}$), deposited at the CNCM (Paris, France) on Mar. 18, 2004 under number CNCM I-3190, or construct pTRACE5-HPV16E7$_{49-57}$. These vectors have been described in WO 2005/089792 and in the examples of the present application.

According to a particular embodiment of the invention, the polypeptide included in the recombinant CyaA is the E7 protein, especially the E7 protein of HPV16, inserted between codons 224 and 235 of CyaA or between codons 319 and 320 of CyaA.

In another embodiment, the recombinant protein of the invention comprises multiple polypeptides, some of which being polypeptides bearing an epitope or several epitopes of one or several HPV, and other polypeptides bearing epitopes of other tumor-associated antigens.

In another particular embodiment, the recombinant protein of the invention further comprises one or several epitopes originating from a different pathogen agent. Association of epitopes originating from *Chlamydia* or from HIV retrovirus or HPV, HBV, HCV, adenoviruses EBV, herpes virus, HTLV.1 virus and CMV, with epitopes originating from HPV may especially be of interest.

Especially, the cryptic epitopes are contained within an HPV antigen, in particular HPV16 and/or HPV18 antigens, especially an E7 antigen.

The recombinant protein thus defined especially comprises a peptide derived from HPV18 E7 protein, i.e., having amino acid sequence IDGVNHQHL (SEQ ID NO: 3).

The invention also concerns peptides having substitutions in this sequence, especially at positions 1 and/or 2, in particular peptides having sequence (I/A)(D/S)GVNHQHL (SEQ ID NO: 4) wherein one or two of the residues at positions 1 and 2 have either of the described meanings.

According to a particular embodiment the cryptic epitope can be modified for example can have substitutions in the two first positions, and for instance can have sequence ASGVN-HQHL (SEQ ID NO: 5).

The invention also comprises variants of said peptides, to the extent that they have immunogenic properties, especially capable of elicitng a T-cell, in particular a CTL response.

Apart from the recombinant protein including CyaA protein or a fragment thereof, one of the further components of the kit of parts or composition according to the invention may be an adjuvant component, suitable for activating the innate immune response primed by a tumor in a patient.

In a particular embodiment of the invention, the adjuvant component is selected in the group of components consisting of nucleic acids, peptidoglycans, carbohydrates, peptides, cytokines, hormones and small molecules, wherein said adjuvant component is capable of signalling through pattern-recognition receptors (PRRs).

PRRs are known to mediate the innate immune response to pathogens, and to tumors, by recognition of so-called evolutionarily conserved signatures from pathogens (pathogen-associated molecule patterns, PAMPs). PRRs are present on a variety of immune cells including dendritic cells, natural killer cells, B cells, and also on some non immune cells such as epithelial cells or endothelial cells. PRRs and their involvement in the innate immune response are described in Pashine A. et al (Nature medicine supplement volume 11, No 4, April 2005).

The kit of parts according to the present invention therefore provides, an adjuvant component for the activation of the innate immune response which targets PRRs and therefore activates signalling through PRRs, wherein said PRRs encompass Toll-like receptors or nucleotide-binding oligomerization domain (NOD) or C type lectin.

In a particular embodiment of the invention, the adjuvant component is a Toll-like receptor agonist.

The Toll-like receptor agonist is especially formulated to efficiently activate the innate immune system of a patient.

Said TLR agonist is capable of binding the TLR, i.e., is a ligand of the TLR and is furthermore capable of enhancing the immune response elicited under the control of said TLR.

For illustration, TLR agonists are selected from the group of TLR-9, TLR-8, TLR-3 and TLR-7 agonists. However agonists of other TLR receptors may be used to perform the invention, such as agonists of the TLR2, TLR4, TLR5, . . . receptors.

The TLR agonist used in the invention can be a natural or a synthetic agonist. It can be a combination of different agonists of the same or of different toll-like receptors.

According to a particular embodiment of the invention, the TLR agonist is an immunostimulatory nucleotide sequence, especially a stabilized nucleotide sequence, for example stabilized as a result of structure modification such as phosphorothioate modification. The nucleotide sequence can also be protected against degradation by specific formulation. Especially liposome formulation thereof, e.g. liposome suspension, can be advantageous for the efficient administration of the immunostimulatory nucleotide sequence.

In a particular embodiment of the invention, the immunostimulatory nucleic acid sequence is a single-stranded RNA.

In a particular embodiment of the invention, the immunostimulatory nucleotide sequence comprises a CpG motif and especially is a CpG oligonucleotide (CpG ODNs).

As an example of suitable CpG oligonucleotides the invention provides TLR-9 ligands such as Type A CpG ODN, i.e., CpG 2216 having nucleotide sequence 5'-GGGGGAC-GATCGTCGGGGGG-3' (SEQ ID NO: 6) or Type B CpG ODN, i.e., CpG 1826 having nucleotide sequence 5'-TCCAT-GACGTTCCTGACGTT-3' (SEQ ID NO: 7).

CpG oligonucleotide can be used after being complexed with DOTAP (Roche Manheim, Germany), in order to protect it against degradation and to facilitate its uptake.

According to another particular embodiment of the invention, the TLR agonist is a small molecule.

Small molecules suitable as TLR agonists are for example imidazoquinoline amine derivatives, such as the one named R848 (resiquimod), i.e., 4-amino-2-ethoxymethyl-a,a, dimethyl-1-H-imidazo[4,5c]quinoline-1-ethanol available from Invivogen, as TLR-7 ligand, or the one named R837 (imiqimod) available from Aldara as TLR-7 agonist.

Other molecules suitable as TLR agonists are polyuridine (pU) as TLR-3 ligand, or polycytidylic acid (PIC) as TLR-7 ligand.

These molecules can be formulated to facilitate their uptake and/or to protect them from degradation.

These molecules can also be prepared as a liposome formulation, especially as a liposome suspension, for administration to a patient.

According to another particular embodiment of the invention, adjuvant component can be a cell-based adjuvant component. Example thereof is dendritic cells that are known to be able to prime lymphocyte response, such dendritic cells being possibly conditioned ex vivo prior to their administration, in order to increase their activity of stimulation of the T cell response. Dendritic cells can hence be stimulated with adjuvants interacting with the PRRs, including TLR ligands or agonists (Pashine A. et al Nature Medicine Supplement Volume 11, No 4, April 2005 p S63-S68)

Apart from the possible presence of a TLR agonist or other adjuvant, the kit of parts of the invention also comprises an agent or molecules suitable for cell response in a patient, in particular by lowering or blocking regulatory T cells immunosuppressive capacity.

According to a particular embodiment of the invention, such an effect on a regulatory cell response may be obtained with an agent modulating a regulatory T cell and/or modulating another cell suppressive response, such as the myeloid suppressive cells response, said agent targeting said regulatory cells, especially T cells, by depleting or inactivating these cells (such as with CD25-specific antibody, or cyclophosphamide), altering trafficking of said cells, especially regulatory T cells (such as CCL22-specific antibody) or altering differentiation and signalling of said cells (such as by blocking FOXP3 (forkhead box P3) signal).

According to a particular embodiment of the invention, the agent modulating a regulatory cell response targets suppressive molecules, especially such molecules present on APCs (such as B7-H1, B7-H4, IDO (indoleamine 2,3-dioxygenase) or arginase) or on T cells (such as CTLA4 (cytotoxic T-lymphocyte-associated antigen 4) or PD1 (programmed cell death 1)), or targets soluble immunosuppressive molecules (such as TGF beta (transforming growth factor), IL-10, VEGF (vascular endothelial growth factor), COX2 (cyclooxygenase 2)).

As examples of agents having an effect on a regulatory cell response, cytotoxic agents are proposed, that can kill Treg cells or other immunosuppressive cells, or that can block their activity and/or development and/or accumulation.

In a particular embodiment of the invention, the agent modulating the regulatory cell response, especially a regulatory T cell response, is a chemotherapeutic agent. Especially it is selected among chemotherapeutic agents known as anti-cancer agents and used in chemotherapy. Such agents include those helping to reduce the tumor burden, those acting by increasing sensitivity of tumor cells to treatment or those enabling killing or inactivating immune regulatory cells. The chemotherapeutic agents used within the frame of the invention thereby enhance antitumor immunity.

In a particular embodiment of the invention, the chemotherapeutic agent is an alkylating agent. Especially, it is Cyclophosphamide (CTX) (Sigma, Steinheim, Germany). Cyclophosphamide is capable of depleting or inactivating regulatory T cells.

In another particular embodiment of the invention, the chemotherapeutic agent is an intercalating agent.

In a particular embodiment, the chemotherapeutic agent is Doxorubicin (DOX) (Calbiochem, La Jolla, Calif., USA).

The chemotherapeutic agent is advantageously administered by low doses.

The various types of molecules described herein to carry out the invention used, in association in a kit of parts, are presented and therefore administered separately, but either simultaneously in time (especially for the recombinant protein and the TLR agonist) or separately in time (especially for the recombinant protein and the chemotherapeutic agent).

In a particular embodiment of the invention, when the kit of parts comprises the use of both the recombinant protein and the chemotherapeutic agent, this agent is administered prior to the recombinant protein acting as therapeutic vaccine. For illustration, the chemotherapeutic agent is given 24 h before the vaccine is administrated.

The administration of the chemotherapeutic agent can alternatively be carried out prior and after the administration of the recombinant protein and/or the TLR agonist. It can also be sequential in time.

A particular regimen that may be adopted with the kit of parts or the composition of the invention, is its use in a repeated administration protocol, especially in a protocol which encompasses two rounds or more of administration of at least one of the compounds of the kit of parts or composition.

The compounds of the kit of parts or the composition of the invention can especially be given to the patient through intravenous administration, intratumoral administration or subcutaneous administration.

The kit of parts of the invention or the composition has the ability to target (i) the adaptive immune response, through the recombinant protein involving recombinant CyaA or a fragment thereof disclosed in the present application, (ii) to downregulate the regulatory immune response through the chemotherapeutic agent, and if the adjuvant is present, to target (iii) the innate component of the immune response, by activating said innate response through the adjuvant.

The inventors have especially shown that the associated use of the three compounds, i.e., the recombinant protein(s), the adjuvant component (for example the TLR agonist) and the agent for modulating the regulatory immune response (for example the chemotherapeutic agent) would enable improvement of the condition of a patient suffering from established tumor, including vascularized or infiltrating tumors or metastatic tumors, occurring for example in situations of advanced cancer and possibly could enable eradication of such tumor and/or metastases. It has especially been observed that the kit of parts according to the invention may be more appropriate to treat later stage of tumor growth than the vaccine constituted of the recombinant protein alone, or agent altering regulatory T cell immune response such as a chemotherapeutic agent alone, or adjuvant of the innate response such as TLR used alone.

The invention also relates to a method of treatment of a patient in need thereof, either a human or an animal patient, comprising the step of administering the components of the kit of parts or of the composition herein disclosed.

It is especially provided that in a particular embodiment of the invention, the kit of parts or the composition or the method of treatment of a human or animal patient is intended and suitable for the treatment of infiltrating or vascularized tumors versus superficial tumors or for the treatment of metastatic tumors versus primary tumors, in accordance with the acknowledged clinical criteria for the classification of tumors.

Solid tumors are especially a target for the treatment through the use of the compounds of the kit of parts or composition of the invention.

Among tumors which may be candidates for the treatment with the kit of parts or with the composition of the invention, the following, for which tumor-associated antigens have been characterized, are described as examples:

Melanoma, especially metastatic melanoma; Lung carcinoma; Head & neck carcinoma; cervical carcinoma, Esophageal carcinoma; Bladder carcinoma, especially infiltrating Bladder carcinoma; Prostate carcinoma; Breast carcinoma; Colorectal carcinoma; Renal cell carcinoma; Sarcoma; Leukemia; Myeloma. For these various histological types of cancers, it has been shown that antigenic peptides are specifically expressed on tumor samples and are recognized by T cells, especially by $CD8^+$ T cells or $CD4^+$ T cells.

A review of peptides found as tumor-associated antigens in these types of tumors is made by Van der Bruggen P. et al (Immunological Reviews, 2002, vol 188:51-64). Especially, the disclosure of the peptides contained in table 3 of said review is referred to herein as providing examples of such tumor-associated antigens and said table 3 is incorporated by reference to the present publication.

The following antigens are cited as examples of tumor-associated antigens recognized by T cells, according to the publication of Kawakami Y. et al (Cancer Sci, October 2004, vol. 95, no. 10, p 784-791) that also provides methods for screening these antigens or further one: antigens shared by various cancers, including MAGE (especially in Melanoma), NY-ESO-1, Her2/neu, WT1, Survivin, hTERT, CEA, AFP, SART3, GnT-V, antigens specific for some particular cancers such as βbeta-catenin, CDK4, MART-2, MUM3, gp100, MART-1, tyrosinase for Melanoma; bcr-abl, TEL-AML1 for Leukemia; PSA, PAP, PSM, PSMA for prostate cancer; Proteinase 3 for myelogenous leukemia; MUC-1 for breast, ovarian or pancreas cancers; EBV-EBNA, HTLV-1 tax for lymphoma, ATL or cervical cancer; mutated HLA-A2 for Renal cell cancer; HA1 for leukemia/lymphoma. Tumor-associated antigens in animals have also been described such as Cycline D1 and Cycline D2 in tumors affecting cats or dogs.

Tumor-associated antigens recognized by T cells have also been disclosed in Novellino L. et al (Immunol Immunother 2004, 54:187-207 and are updated on the following site: http://www.istitutotumori.mi.it/INT/AreaProfessionale/Human_Tumor/pdf/human_tumor_antigens.pdf.

More generally, TAA of interest in the present invention are those corresponding to mutated antigens, antigens that are overexpressed on tumor cells, shared antigens, tissue-specific differentiation antigens or viral antigens.

The cited antigens can be candidates for preparing recombinant CyaA (including fragments thereof) proteins, for use in the kits of parts or in the compositions of the invention.

Especially, for illustration purposes, it has been shown in the present invention, that adjuvants of the innate immune response, especially TLR agonists, increase the therapeutic effect of the recombinant protein disclosed herein on advanced tumors, occurring after HPV infection, especially when the recombinant protein bears an E7 antigen or fragment thereof as defined in the present application. Some TLR ligands associated with CyaA recombined with a tumor-associated antigen, significantly increased the percentage of large-tumors regression. Furthermore, it has been shown that low doses of cyclophosphamide can control the number and activity of regulatory T cells (Treg) (13).

The kit of parts or the composition is considered to achieve the therapeutic effect which is sought if the size of the tumor or associated metastases of the treated patient is blocked or reduced, transiently or definitely, and more preferably is eradicated.

Other features and properties of the invention are disclosed in the following examples and figures.

FIGURES

FIG. 1. FIGS. 1.1 (A to H): Abrogation of CyaA-E7 therapeutic effects in large tumor-bearing mice. C57BL/6 mice were inoculated on day 0 with $5 \times 10^5$ TC-1 cells and then received PBS at day 4 (A) or were treated i.v. with 50 μg of CyaA-E7 at day 4 (B), 7 (C), 11 (D), 18 (E), 25 (F) or 30 (G). Each curve represents the mean diameter of the tumor in a single mouse. The number of tumor free mice on day 100 versus the total number of animals included, the percentage of survival on day 100 and the p-value of the Likelihood Ratio test to compare the tumor growth versus the tumor growth in the PBS-treated group are shown. H) Kaplan-Meier plot of mice survival. Mice were sacrificed when tumor diameter reached 20 mm or whenever the sanitary status of the animals commanded. Pooled data of two independent experiments are shown;

FIG. 1.2.CTX effect on tumor growth in $RAG^{-/-}$ mice. A, C57BL/6-RAG-$1^{-/-}$ mice were injected on day 0 with $5 \times 10^5$ TC-1 cells. On day 24, they received 2.5 mg CTX i.p. or 200 μl PBS. The number of tumor-free mice on day 60 relating to the total number of animals included, the percent surviving on day 60 and the p-value determined by likelihood ratio test comparing tumor growth in the CTX-treated groups with tumor growth in the PBS-treated group are indicated for each set of experiments. B, Kaplan-Meier plot of mouse survival. The log-rank test was used to compare the group receiving CTX with the group treated with PBS (p=0.22). Mice were killed when tumor diameter reached 20 nm or when necessary due to the sanitary status of the animals. Pooled data of two independent experiments are shown.

FIG. 2. FIG. 2.1 Combined tumor treatment with CyaA-E7 and different TLR-ligands. C57BU/6 mice were inoculated on day 0 with $5 \times 10^5$ TC-1 cells. On day 25, they received either PBS (A), 50 μg of CyaA-E7 alone (B), 30 μg of CpG-B complexed with 60 μg of DOTAP (C), or 25 μg of PIC (D) or they were injected i.v with 50 μg of CyaA-E7 combined with 50 μg of R848 (E), or with 30 μg of pU/DOTAP (F), of CpG-A/DOTAP (G) or of CpG-B/DOTAP (H), or with 25 μg of PIC (I). Each curve represents the mean diameter of tumor in a single mouse. The number of tumor free mice on day 100 versus the total number of animals included, the percentage of survival on day 100 and the p-value of the Likelihood Ratio test to compare the tumor growth versus the tumor growth in the CyaA-E7-treated group or versus the tumor growth in the PBS-treated group are shown. J) Kaplan-Meier plot of mice survival. Mice were sacrificed when tumor diameter reached 20 mm or whenever the sanitary status of the animals commanded. Pooled data of two independent experiments are shown.

FIG. 2.2. Evaluation of CTX doses. A, C57BL/6 mice were injected on day 0 with $5 \times 10^5$ TC-1 cells. On day 24, they were left untreated or received 100 mg/kg or 300 mg/kg of CTX i.p. On day 25, mice were injected with PBS or 50 μg CyaA-E7. The number of tumor-free mice on day 75 relative to the total number of animals included, the percent surviving on day 75 and the p-value determined by likelihood ratio test comparing tumor growth in the group treated with 300 mg/kg CTX with tumor growth in the group treated with 100 mg/kg CTX are indicated for each set of experiments. B, Kaplan-Meier plot of mouse survival. The log-rank test was used to compare the group receiving 300 mgkg CTX with the group receiving 100 mg/mg CTX (p=0.95). Mice were killed when tumor diameter reached 20 mm or when necessary due to the sanitary status of the animals. Pooled data of two independent experiments are shown.

FIG. 3. Combined tumor treatment with CyaA-E7 and chemotherapy agents. C57BL/6 mice were inoculated on day 0 with $5 \times 10^5$ TC-1 cells. On day 24, mice were left untreated (A, B) or received either 2.5 mg cyclophosphamide (CTX) i.p (C, D) or 125 μg doxorubicin (DOX) i.t. (E). On day 25, mice received i.v either PBS (A, C) or 50 μg of CyaA-E7 (B, D, E). The number of tumor free mice on day 100 versus the total number of animals included, the percentage of survival on day 100 and the p-value of the Likelihood Ratio test to compare the tumor growth versus the tumor growth in the CyaA-E7-treated group or versus the tumor growth in the PBS-treated group are shown. F) Kaplan-Meier plot of mice survival. Mice were sacrificed when tumor diameter reached 20 mm or whenever the sanitary status of the animals commanded. Pooled data of two independent experiments are shown.

FIG. 4. Combined tumor treatment with CyaA-E7, CpG-B/DOTAP and CTX (tritherapy). C57BL/6 mice were inoculated on day 0 with $5 \times 10^5$ TC-1 cells and on day 24, they were left untreated (A, B) or received 2.5 mg CTX i.p (C, D). On day 25, they were injected i.v either with PBS (A), 50 μg of CyaA-E7 (B), CpG-B/DOTAP (C) or with 50 μg of CyaA-E7 and 30 μg of CpG-B/DOTAP (D). The number of tumor free mice on day 100 versus the total number of animals included, the percentage of survival on day 100 and the p-value of the Likelihood Ratio test to compare the tumor growth versus the tumor growth in the CyaA-E7-treated group or versus the tumor growth in the PBS-treated group are shown. E) Kaplan-Meier plot of mice survival. Mice were sacrificed when tumor diameter reached 20 mm or whenever the sanitary status of the animals commanded. Pooled data of two independent experiments are shown.

FIG. 5. FIG. 5.1 The therapeutic efficacy of tritherapy decreases in advanced tumors. C57BL/6 mice were inoculated on day 0 with $5 \times 10^5$ TC-1 cells and were left untreated (A, B) or received 2.5 mg CTX i.p on day 24 (C), 29 (D) or 39 (E). On day 25, control mice were injected either with PBS (A) or with 50 μg of CyaA-E7 alone (B). On day 25 (C), 30 (D) or 40 (E), groups of mice were treated i.v with 50 μg of CyaA-E7 and 30 μg CpG-B/DOTAP. The number of tumor free mice on day 100 versus the total number of animals included, the percentage of survival on day 100 and the p-value of the Likelihood Ratio test to compare the tumor growth versus the tumor growth in the tritherapy group are shown. F) Kaplan-Meier plot of mice survival. Mice were sacrificed when tumor diameter reached 25 mm or whenever the sanitary status of the animals commanded. Pooled data of two independent experiments are shown.

FIG. 5.2. Antitumoral efficacy of a second administration of tritherapy. A, C57BL/6 mice were injected on day 0 with $5 \times 10^5$ TC-1 cells. On day 39, they were left untreated or received 2.5 mg CTX i.p. On day 40, control mice were injected with PBS and mice treated with tritherapy were injected i.v with 50 μg CyaA-E7 and 30 μg CpG-B/DOTAP. A group of mice were also treated with CTX on day 54 and with CyaA-E7 and CpG-B/DOTAP on day 55. The number of tumor-free mice on day 90 after treatment relative to the total number of animals included, the percent surviving on day 90 after treatment and the p-value determined by likelihood ratio test comparing tumor growth in the groupe treated with tritherapy on day 40 with tumor growth in the PBS-treated group or the group treated with tritherapy on days 40 and 55 versus the group treated with tritherapy on day 40 are indicated for each set of experiments. B, Kaplan-Mier plot of mouse survival. The log-rank test was used to compare the group receiving tritherapy on day 40 with the group treated with PBS (p<0.0001) and the group treated on days 40 and 55 with the group treated on day 40 (p=0.0012). Mice were killed when tumor diameter reached 20 nm or when necessary due to the sanitary status of the animals. Pooled data of two independent experiments are shown.

FIG. 6. Evaluation of the tritherapy in the EL4-E7 model. C57BL/6 mice were inoculated on day 0 with $4 \times 10^6$ EL4-E7 cells and were left untreated (A) or received 2.5 mg CTX i.p on day 6 (B), 13 (C) or 20 (D). Mice were injected i.v either with PBS on day 25 (A) or 50 μg of CyaA-E7 and 30 μg CpG-B/DOTAP on day 7 (B), 14 (C) or 21 (D). The number of tumor free mice on day 100 versus the total number of animals included, the percentage of survival on day 100 are shown. E) Kaplan-Meier plot of mice survival. Mice were sacrificed when tumor diameter reached 25 mm or whenever the sanitary status of the animals commanded. Pooled data of two independent experiments are shown.

Figure 7B:
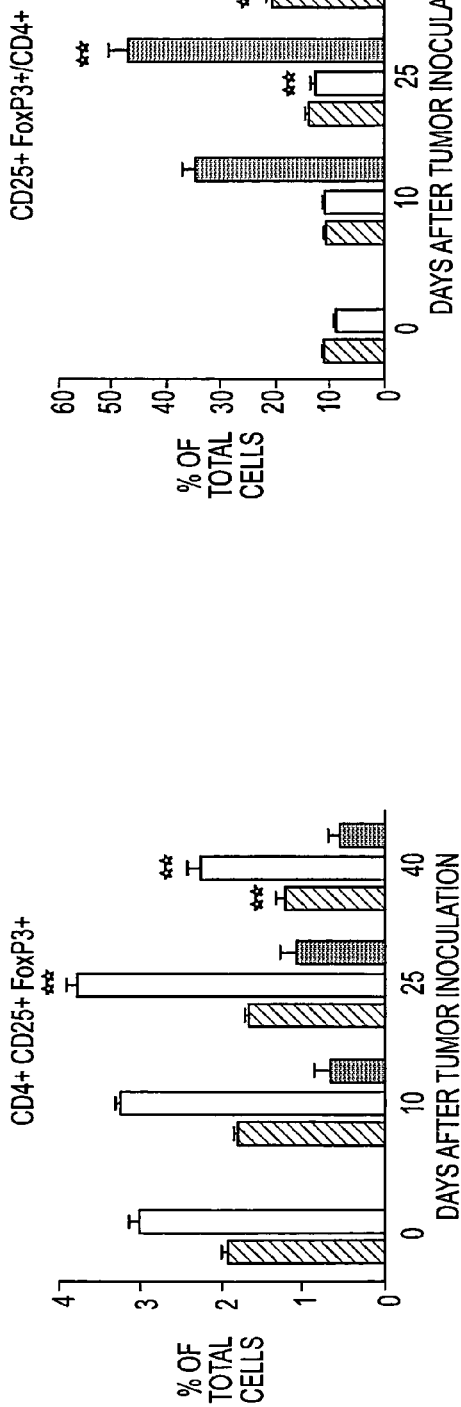
Figure 7C:
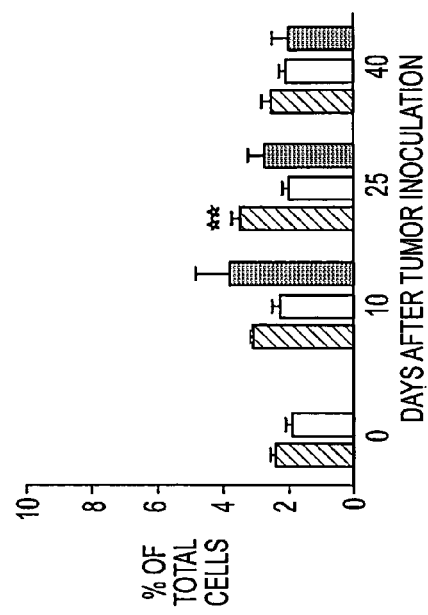

FIG. 7. Changes in immune cells after tumor inoculation. C57BL/6 mice were inoculated on day 0 with $5 \times 10^5$ TC-1 cells and three mice were sacrificed on days 0, 10, 25 and 40. Spleen, tumor draining lymph nodes and tumor were excised, ground to prepare the cell suspensions, stained and analyzed by flow cytometry. Pooled data of two experiments are shown (n=6-9 mice). Bars represent mean values and the error bars correspond to standard error of the mean. *<0.05**<0.01. A) Percentage of $CD4^+$ $CD25^+FoxP3^+$ cells. B) Percentage of $CD4^+$ cells that express CD25 and FoxP3. C) Percentage of $CD11c^+$ cells. D) Percentage of $CD11b^+$ cells. E) Percentage of $GR1^+$ cells. F) Percentage of $CD11b^+GR1^+$ positive cells.

FIG. 8. Analysis of tumor specific immune response in control and tumor-bearing mice after different treatments. C57BL/6 mice were left untreated (A, C) or were inoculated on day 0 with $5 \times 10^5$ TC-1 cells (B, D). Twenty-five days later, control and tumor-bearing mice were injected with either 50 μg of control CyaA or of CyaA-E7, with PBS or with 30 μg of CpG-B or pU/DOTAP, 25 μg of PIC, 50 μg of R848, 2.5 mg of CTX (24 h before) or with CTX and CpG-B/DOTAP. Percentage of $CD8^+$ tetramer$^+$ cells in control (A) and in tumor-bearing mice (B). At day 7 after treatment, mice were sacrificed and the percentage of tetramer positive cells was analyzed by flow cytometry. In vivo CTL in control (C) and in tumor-bearing mice (D). At day 7 after treatment, mice were i.v. injected with $5 \times 10^6$ splenocytes loaded with $CFSE^{high}$ and $E7_{49-57}$ peptide and with $5 \times 10^6$ splenocytes loaded with $CFSE^{low}$. Twenty-four hours later, spleens were removed and single-cell suspensions were analyzed by flow cytometry to determine the ratio of $CFSE^{high}$ to $CFSE^{low}$ cells. Pooled data of two experiments are shown (n=6). Bars represent mean values and the error bars correspond to standard error of the mean. Data was compared by ANOVA followed by Dunnett post test. In vivo cytolytic activity was low but detected (E and F).

FIG. 9. Changes in immune cells after tritherapy on day 25. C57BL/6 mice were inoculated on day 0 with $5 \times 10^5$ TC-1 cells. On day 24, they received 2.5 mg CTX i.p and 24 h after, 50 μg of CyaA-E7 and 30 μg CpG-B/DOTAP. Groups of mice were sacrificed before treatment (day 0), 24 hour after CTX alone (day 1) or on days 4, 7 or 11 after tritherapy administration. Spleen, tumor draining lymph nodes and tumor were excised, ground to prepare the cell suspensions, stained and analyzed by flow cytometry. Pooled data of two experiments are shown (n=4-6 mice). Bars represent mean values and the error bars correspond to standard error of the mean. *<0.05**<0.01. A) Percentage of $CD4^+$ cells that express CD25 and FoxP3. B) Percentage of $CD4^+$ cells that are $CD25^-$ and $FoxP3^+$. C) Percentage of $CD4^+$ cells that express FoxP3. D) Percentage of $CD8^+$ cells that are tetramer$^+$ and $CD44^+$. E) Percentage of $CD11c^+$ cells. F) Percentage of $CD11b^+$ cells. G) Percentage of $GR1^+$ cells. H) Percentage of $CD11b^+GR1^+$ positive cells.

Figure 10:
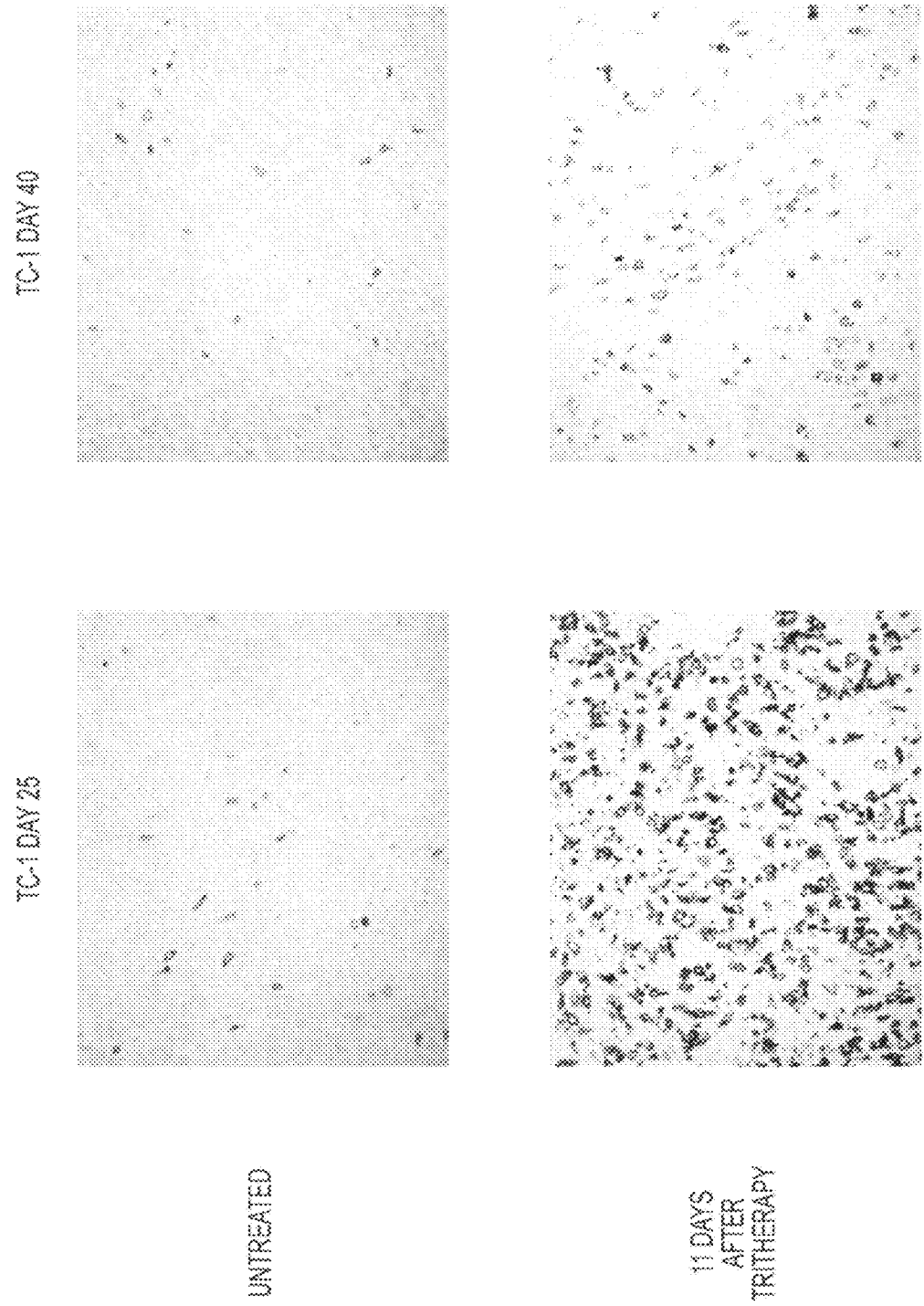

FIG. 10. Immunostaining of CD3. C57BL/6 mice were injected on day 0 with $5 \times 10^5$ TC-1 cells. On day 24 or 39, they received 2.5 mg CTX i.p. On day 25 or 40, mice were treated i.v with 50 μg CyaA-E7 and 30 μg CpG-B/DOTAP. Eleven days after treatment, mice were sacrificed. Non-treated tumor-bearing mice were sacrificed on days 25 and 40. Immunostaining of tumors for CD3 was done as described in Materials and Methods.

Figure 11A:
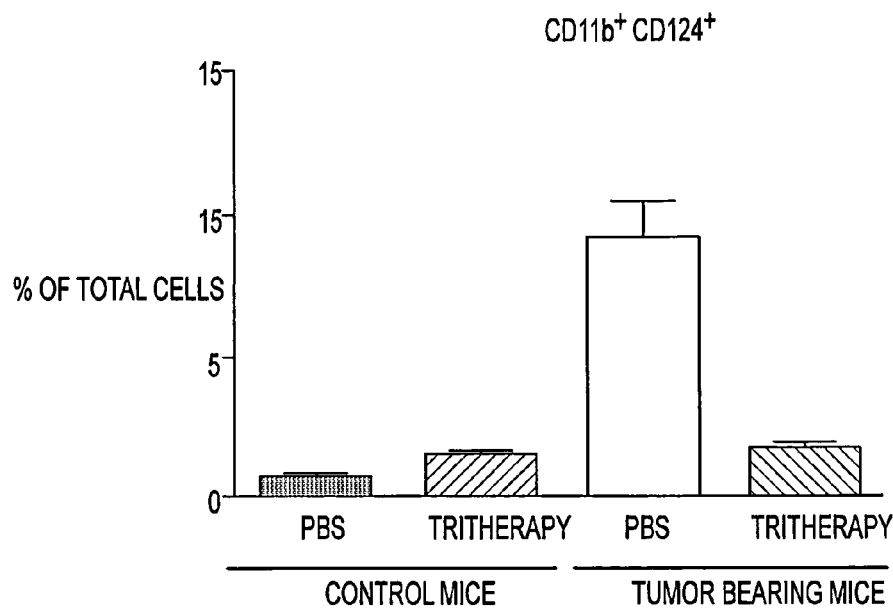
Figure 11B:
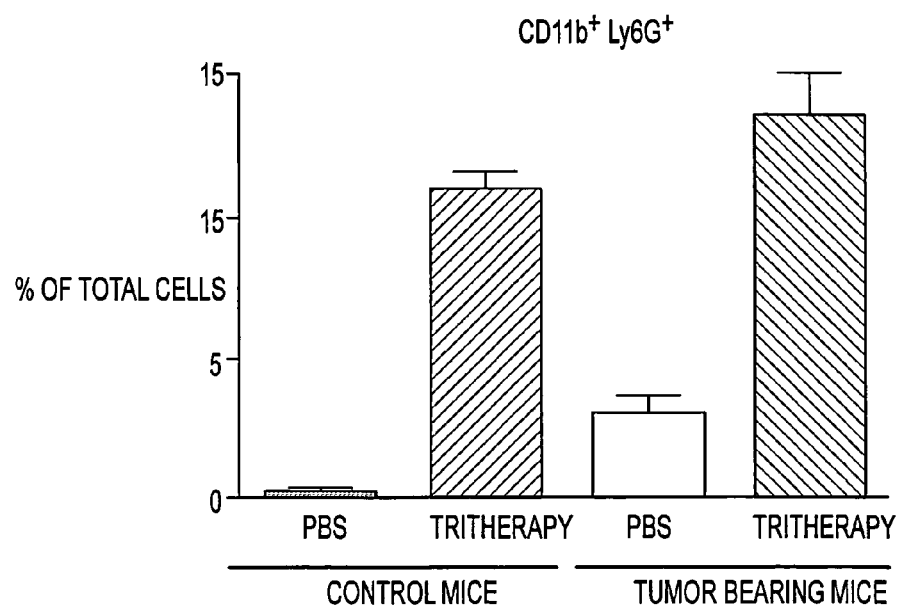

FIG. 11. Phenotype of myeloid cells induced by tritherapy and by tumor growth. C57BL/6 mice were injected on day 0 with 5×10$^5$ TC-1 cells. Tritherapy treated mice received on day 24, 2.5 mg CTX i.p and 24 h later, 50 μg CyaA-E7 and 30 μg CpG-B/DOTAP. PBS treated mice received 200 μl of PBS on day 25. Control mice without tumors received similar treatments. All mice were sacrificed 11 days after treatment (36 days after tumor inoculation). Spleens were excised, ground to prepare the cell suspensions, stained and analyzed by flow cytometry. A representative experiment of two is shown (n=6 mice). Bars represent mean values and the error bars correspond to standard error of the mean. The percentages of CD11b$^+$CD124$^+$ and CD11b$^+$Ly6G$^+$ cells are presented in panels A and B, respectively.

EXAMPLES

A tritherapy based on the simultaneous targeting of innate (by a TLR9 ligand), adaptive (by the CyaA-E7) and regulatory (by low dose of cyclophosphamide) component of the immune system was shown to induce full eradication of large-tumor in around 90% of treated animals.

Materials and Methods

Mice and Tumors

Specific pathogen-free 5-week-old female C57BL/6 mice were purchased from Charles River (L'Arbresle, France) and were kept in the Pasteur Institute animal facilities under pathogen-free conditions with water and food ad libitum. C57BL/6-RAG1$^{-/-}$ mice were obtained from the Jackson Laboratory, USA. Experiments involving animals were conducted according to the institutional guidelines for animal care.

TC-1 cells expressing HPV16-E6 and HPV16-E7 proteins derived from primary mouse lung epithelial cells were obtained from the American Type Culture Collection (LGC Promochem, Molsheim, France) (14). EL4-E7 cells, a mouse lymphoma expressing HPV16-E7 (15). Cells were maintained in RPMI 1640 with GlutaMAX supplemented with 10% heat-inactivated fetal calf serum, 100 units/ml penicillin, 100 μg/ml streptomycin, 0.4 mg/ml geneticin and 5×10$^{-5}$ mol/l 2-mercaptoethanol (Life Technologies, Cergy-Pontoise, France).

Tumor cells lines (5×10$^5$ TC-1 cells or 4×10$^6$ EL4-E7 cells) were inoculated into the shaved left back of C57BL/6 mice in 200 μl volume of PBS. Tumor size, presented as the average of two perpendicular diameters (millimeters), was measured at regular intervals.

Reagents

The synthetic peptide E7$_{49-57}$ (RAHYNIVTF (SEQ ID NO: 1), one-letter code for amino acid) corresponding to the HPV16-E7 H2-D$^b$-restricted epitope (16) was purchased from NeoMPS (Strasbourg, France).

The detoxified form of the adenylate cyclase of Bordetella pertussis carrying a truncated form of the E7 protein (CyaA-E7) and the control adenylate cyclase without any insert (CyaA) were purified as described in (5) and as summarized hereafter.

CpG ODNs (Type A, CpG 2216: 5'-GGGGGAC-GATCGTCGGGGGG-3' (SEQ ID NO: 6); Type B, CpG 1826: 5'-TCCATGACGTTCCTGACGTT-3' (SEQ ID NO: 7)) were synthesized by Proligo (Paris, France). Boldface nucleotides correspond to phosphorothioate backbone. Polyuridine (pU) was purchased from Sigma (Steinheim, Germany), R848 from PharmaTech (Shanghai, China) and polyinosinic-polycytidylic acid (PIC) from Invivogen (San Diego, Calif., USA). Thirty μg of CpG ODNs or pU were diluted in 50 μl of Optimen medium (Gibco, Grand Island, N.Y., USA) and mixed with 60 μg of DOTAP (Roche, Mannheim, Germany) diluted in 100 μl of Optimen. The rest of the reagents were diluted in PBS before injection. Cyclophosphamide (CTX) (Sigma, Steinheim, Germany) and doxorubicin (DOX) (Calbiochem, La Jolla, Calif., USA) were diluted respectively in PBS and in sterile water before injection. The different antigenic formulations and adjuvants were injected simultaneously except chemotherapeutic agents that were given 24 h before vaccine. Intravenous administrations were performed by retroorbital injection in a volume of 200 μl, intratumoral administrations were done by injection in a volume of 50 μl and subcutaneous administration were performed in 200 μl.

Construction and Purification of Recombinant B. Pertussis Adenylate Cyclase Carrying HPV16-E7 Epitopes.

Recombinant adenylate cyclase used were expressed in E. coli by using derivatives of plasmid pTRACE5 (5) which codes for an enzymatically inactive CyaA (Dadaglio G et al Int Immunol, 15: 1423-1430, 2003) (Gmira S. et al Res Microbiol, 152: 889-900, 2001). Plasmid pTRACE5 is an expression vector for an enzymatically inactive, and therefore non-cytotoxic, variant of B. pertussis CyaA. It also expresses B. pertussis cyaC gene that is required for the postranslational acylation of CyaA. This plasmid is a derivative of the previously described pTRACG plasmid (Gmira et al., 2001, Res. Mic. 152:889). It was obtained by insertion of the hexanucleotide CTGCAG in the EcoRV site located within the 5' part of the cyaA DNA sequence. This results in an in-frame insertion of the dipeptide Leu-Gln between Asp188 and IIe189 of CyaA within an essential part of the catalytic site (Guermonprez et al. 2000, Meth. Enzymol. 326:527).

Plasmid pTRACE5 harbors a ColE1 origin of replication and an Ampcillin resistant marker. In this plasmid, the cyac and the modified cyaA genes are placed in the same transcriptional unit under the control of the λ phage Pr promoter. The pTRCAG plasmid also encodes the thermosensitive λ repressor cI$^{857}$ that strongly represses gene transcription at the λ Pr promoter at temperatures below 32° C.

The E. coli strain XL1-Blue (Stratagene, La Jolla, Calif.) was used for all DNA manipulations that were performed according to standard protocols (Maniatis et al.).

CyaA E7$_{49-57}$ contains a 9-amino acid long polypeptide sequence (RAHYNIVTF (SEQ ID NO: 1)) inserted between codons 224 and 235 of CyaA. The expression plasmid for CyaA-E7$_{49-57}$ was constructed as follows. Two synthetic oligonucleotides (MWG, Courtabceuf, France), BTP1 (5'-CTA GCC GTG CCC ATT ACA ATA TTG TAA CCT TTG GTA C-3' (SEQ ID NO: 8) coding strand) and BTP2 (5'-CAA AGG TTA CAA TAT TGT AAT GGG CAC GG-3' (SEQ ID NO: 9) non coding strand) were annealed and ligated into the pTRACE5 digested with NheI and KpnI. CyaA-E7$_{Full}$ contains the entire sequence of the HPV16-E7 protein, i.e., 98 amino acids, inserted at the same 224 position of the enzymatically inactive CyaA deposited at the CNCM (Paris, France) under n° CNCM I-3191 on Mar. 18, 2004. The DNA sequence encoding the E7 protein was amplified from HPV16 DNA (Seedorf K et al Virology 145: 181-185, 1985) using specific primers BTP3, (5'-GGG CGC TAG CAT GCA TGG AGA TAC ACC TAC-3' (SEQ ID NO: 10)), and BTP4 (5'-

GGG CGG TAC CTG GTT TCT GAG AAC AGA TGG G-3' (SEQ ID NO: 11)). The resulting PCR product was digested by NheI and KpnI and ligated into pTRACE5 cleaved by NheI and KpnI. The SspI site present in the annealed oligonucleotide as well as in the full sequence of HPV16-E7 allowed rapid identification of insertion mutants. CyaA-E7$_{\Delta 30\text{-}42}$ contains the first 29 amino acid residues of HPV16-E7 inserted between codons 319 and 320 of CyaA as well as residues 43 to 98 of HPV16-E7 inserted between codons 224 and 235 of CyaA. The expression plasmid for CyaA-E7$_{\Delta 30\text{-}42}$ was constructed in two steps deposited at the CNCM under n° CNCM 1-3190 on Mar. 18, 2004. A first DNA fragment encoding (amino acid residues 1 to 29) of HPV16-E7 was PCR amplified using as a target DNA a synthetic HPV16-E7 gene (optimized for production in *E. coli*, designed by GTP Technology, Labège, France), and primers BTPS (5'-GGG CAC CGG TAA ACG TAT GCA CGG CGA TAC TCC G-3' (SEQ ID NO: 12)), and BTP6 (5'-CGT GAG CAT CTG GCT TTC ACT AGT ACG TTT GTT CAG CTG CTC GTA GCA-3' (SEQ ID NO: 13)). A second, DNA fragment encoding codons 320 to 372 of CyaA was PCR amplified using pTRACE5 as target DNA and primers BTP7 (5'-GGG CAC TAG TGA AAG CCA GAT GCT CAC GCG CGG G-3' (SEQ ID NO: 14)), and BTP8 (5'-AGT ACA TCC GGC GAG AAC-3' (SEQ ID NO: 15)). These two DNA fragments (that partly overlap) were purified and combined with primers BTPS and BTP8 in a third PCR to amplify a 294 bp long DNA fragment. This fragment was digested by AgeI and BstBI and inserted between the corresponding sites of pTRACE5 to yield plasmid pTRACE5-E7$_{1\text{-}29}$. Then, a DNA fragment encoding the amino acid residues 43 to 98 of HPV16-E7 was PCR amplified using the synthetic HPV16-E7 gene as target DNA and primers BTP9 (5'-GGG CGC TAG CGG TCA AGC AGA ACC GGA C-3' (SEQ ID NO: 16)) and BTP10 (5'-GGG CGG TAC CAG GTT TTT GAG AGC AAA TCG GAC AAA CAA TCC CCA GAG TAC CCA TC-3' (SEQ ID NO: 17)). The purified PCR fragment was digested by NheI and KpnI and ligated into plasmid pTRACE5-E7$_{1\text{-}29}$ digested by the same restriction enzymes.

All recombinant adenylate cyclase were produced in the *Escherichia coli* strain BLR (Novagen, Madison, Wis.) as described previously (26). The recombinant proteins were purified close to homogeneity (FIG. 1B) from inclusion bodies by a two-step procedure that includes DEAE-Sepharose and phenyl-Sepharose chromatography, as described previously (26). An additional washing step with 60% isopropanol in 20 mM Hepes-Na, pH7.5, was added to the phenyl-Sepharose chromatography in order to eliminate most of the contaminating LPS. LPS contents were determined using the kit QCL-1000 (Biowhittaker, Walkersville, Md.). Purified recombinant proteins were analyzed by SDS-gel analysis. Protein concentrations were determined spectrophotometrically from the absorption at 280 nm using a molecular extinction coefficient of 142,000 $M^{-1} \cdot cm^{-1}$.

Flow Cytometric Analysis

To analysis cells changes during tumor growth or after therapy, solid tumors, spleens and inguinal lymph nodes were excised, ground to prepare cell suspensions, and subsequently stained.

Monoclonal antibodies used for staining were FITC-conjugated anti-CD11b, anti-CD4, anti-CD69, anti-CD8; PE-conjugated anti-GR1+, anti-CD124 anti-NK1.1; APC-conjugated anti-CD25, anti-CD44, anti-CD69, anti-CD8, anti-CD11c (all from PharMingen, Erembodegem, Belgium). PE-conjugated H-2D$^b$/E7$_{49\text{-}57}$ tetramers were obtained from Beckman Coulter (Fullerton, Calif., USA). T regulatory cells staining was done using Mouse Regulatory Staining kit (E-biosciences, San Diego, Calif., USA).

FACScalibur (Becton Dickinson, Franklin Lakes, N.J., USA) was used for flow cytometry and events were analyzed with CELLQuest software (Becton Dickinson, Franklin Lakes, N.J., USA).

In Vivo Killing Assay

Naïve spleen cells were pulsed for 30 min with 9 µM E7$_{49\text{-}57}$ peptide at 37° C. After extensive washing, cells were labelled with 2.5 µM CFSE (CFSE$^{high}$) (Molecular Probes). Control non-peptide-treated splenocytes were labelled with 0.25 µM CFSE (CFSE$^{low}$). CFSE$^{high}$ and CFSE$^{low}$ cells were mixed in a 1:1 ratio and $10^7$ cells were injected i.v. into naïve or immunized animals. Twenty-four hours later, spleens were removed and single-cells suspensions were analyzed by flow cytometry to determine the ratio of CFSE$^{high}$ to CFSE$^{low}$ cells. The percentage of specific lysis was calculated as follow: percent-specific lysis=100−(100×(% CFSE$^{high}$immunized/% CFSE$^{low}$ immunized)/(% CFSE$^{high}$ control/% CFSE$^{low}$ control)).

Anti-CD3 Immunohistochemistry

Tumor samples were fixed for formalin and embedded in paraffin. Three-micrometer sections were microwaved for 10 minutes in Tris-EDTA (0.001 M pH 9) for antigen retrieval and endogenous peroxidase was quenched with Peroxidase Blocking Reagent (Dako, Carpintero, Calif.). Tissue sections were incubated overnight at 4° C. with affinity purified anti-human CD3 (Lab Vision Corporation, Fremont, Calif.) diluted 1:300 in tris-buffered saline. The peroxidase activity was revealed using anti-rabbit EnVision System (Dako) and DAB+ Substrate Chromogen System (Dako). Finally, sections were counterstained with methyl green.

Statistical Analysis

Tumor growth data were analyzed by non-linear mixed effect models using Monolix software (http://www.math.u-psud.fr/~lavielle/monolix/). Mean diameters of tumors over time were fitted using the model described in (17) and treatments were compared using the Likelihood Ratio test. Kaplan-Meier plots were used to analyzed survival, and a log rank test was used to examine statistical significance of differences in the survival curves using Prism software (GraphPad Software, Inc. San Diego, USA). Data from in vivo CTL and tetramer staining were compared by ANOVA followed by Dunnett posttest. p values less than 0.05 were considered to be statistically significant.

Results

CyaA-E7 Therapeutic Effect is Abrogated in Large Tumor-Bearing Mice

We have previously shown that a single injection of the CyaA recombinant protein carrying the HPV E7 antigen (CyaA-E7), 10 days after the graft of $5 \times 10^4$ TC-1 tumor cells, induces a full regression of tumor growth and leads to the survival of all treated mice (5). To determine if such therapeutic vaccination is still efficient at later stage of tumor growth, mice were injected with $5 \times 10^5$ TC-1 cells and then treated with a single i.v. injection of 50 µg of CyaA-E7 at various time points. In mice treated 4 days after the injection of TC-1 cells, after an initial phase of growth, tumors were rejected in all animals. Tumor relapse at day 60 was however observed in one mouse (FIG. 1.1B). A progressive decrease of the CyaA-E7 antitumor efficacy was observed in mice, which received a delayed treatment. Thus, only 20% of mice treated by CyaA-E7 25 days after injection of TC-1 cells were protected from tumor growth. However, the delayed in tumor growth and the increased survival were still significant as compared to PBS treated mice (FIG. 1.1F, H). In mice treated 30 days after tumor inoculation, we did not observed any significant difference in the tumor growth or the survival as compared to the PBS-treated group (FIG. 1.1G, H). Thus, when injected one month after the tumor graft, CyaA-E7 lost its capacity to induce therapeutic antitumor responses.

TLR-Ligands Increase the Therapeutic Efficacy of CyaA-E7 on Advanced Tumors

We then tested whether adjuvants can restore the antitumor therapeutic responses induced by CyaA-E7 administration in mice suffering from advanced tumors. For these experiments, mice were treated 25 days after tumor cells injection since it was the latter time point where we could detect the CyaA-E7 therapeutic activity.

Toll-like receptor (TLR) ligands have recently received great attention due to their ability of trigger DC maturation in vivo. We selected for these experiments five synthetic TLR ligands: a TLR-3 ligand, polyinosinic-polycytidylic acid (PIC), two TLR-7 ligands, polyuridine (pU) and R848 and two TLR-9 ligands, CpG-A and CpG-B. pU and CpGs were complexed in DOTAP to protect them from degradation and facilitate their uptake.

Figure 3A:
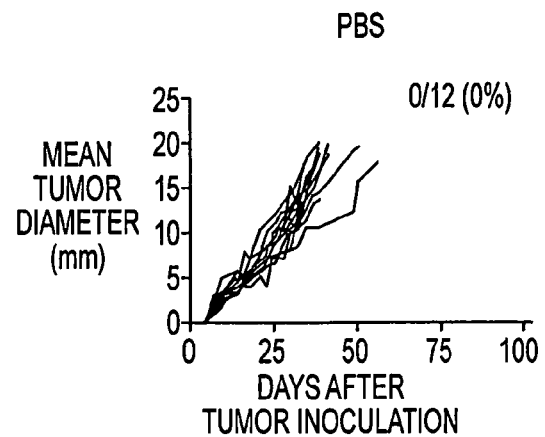
Figure 3B:
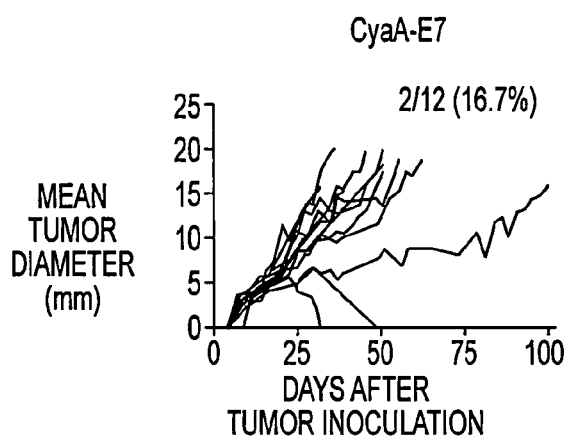
Figure 3C:
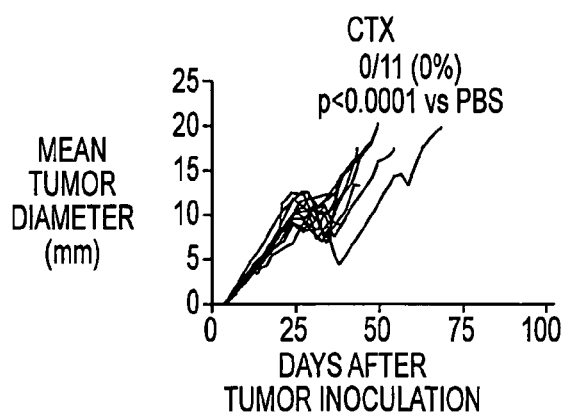
Figure 3D:
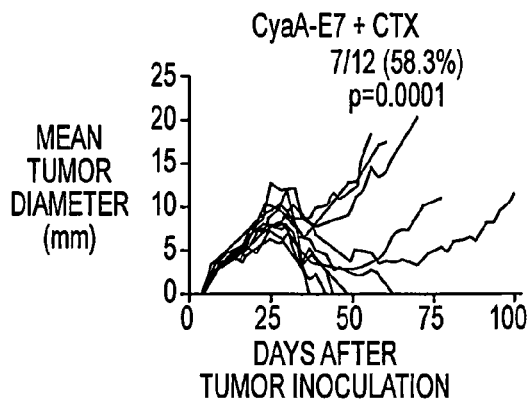
Figure 3E:
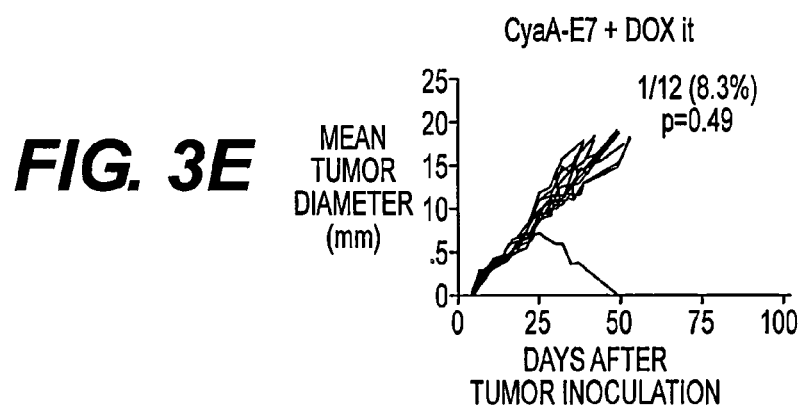
Figure 3F:
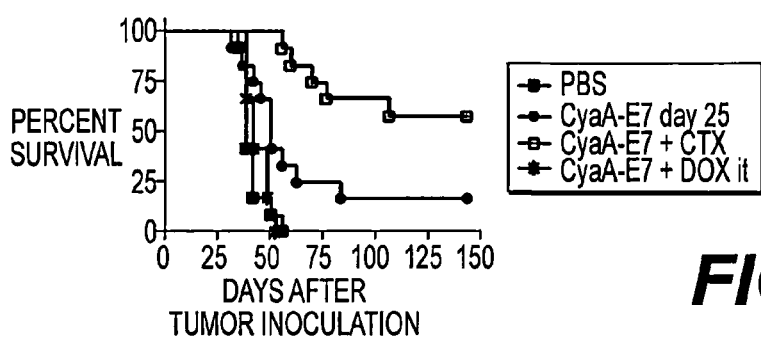

A significant increase in tumor regression was observed in mice treated 25 days after TC-1 cells injection with CyaA-E7 and with pU or CpGs or PIC but not with the R848. The survival percentage ranged from 41% with pU and PIC to 50% with CpG-B and 58% with CpG-A (FIGS. 2.1F, G, H, I and J). After injection of CyaA-E7 with these TLR agonists at day 25, the tumors continued to grow for five to seven days, reaching diameters up to 14 mm. Then, the size of most of the tumors started to decrease, reflecting a successful induction of a therapeutic immune response. This phase could last for 25 days, ultimately leading to the total cure of the tumor. However, in some mice, a tumor relapse was observed before its total eradication. The therapeutic effect of two of these TLR ligands (PIC and CpG-B) administered alone without the CyaA-E7 vaccine was tested to study whether these TLR ligands could enhance the immune response primed by the tumor. However, none of these TLR ligands administered alone had any effect on the tumor growth (FIGS. 2.1C, D and J). Therefore, E7 delivery by the CyaA is required to achieve regression of these large tumors. We then analyzed if chemotherapeutic agents could also restore the therapeutic activity of CyaA-E7 when administered to large-tumor bearing mice. We selected two drugs for this purpose: cyclophosphamide (CTX), an alkylating agent of the nitrogen mustard type that have been shown for a long time to enhance the efficacy of antitumor vaccines (20) (21); and doxorubicin (DOX), an intercalating agent that inhibit the action of the enzyme topoisomerase II and induce an immunogenic cell death that can control the growth of tumors after intratumoral injection (22). In our model of large tumors, DOX did not enhance the effect of CyaA-E7 when given either intra-tumorally (FIGS. 3E, F), or intravenously. In contrast, low dose of CTX injected 24 hours before the CyaA-E7 vaccine led to a delayed growth of all tumors and 58% of mice totally eradicated their tumors. Unlike the TLR ligands, the administration of CTX alone significantly delayed tumor growth but this effect was transient and was followed by tumor relapse (FIG. 3C). This tumor growth delay was not observed in RAG1$^{-/-}$ mice (FIG. 1.2), strongly suggesting that this effect was mediated by T cells. Finally, the antitumor efficacy of the combined administration of CTX and CyaA-E7 was not improved by a threefold CTX dose increase (FIG. 2.2). CTX at 100 mg/kg displayed maximal antitumor efficacy, reducing the possible side-effects associated to this combined therapy.

Eradication of Large Tumors by a Tritherapeutic Treatment Combining Chemotherapy, a TLR-9 Ligand and an Antitumor Vaccine Next, we hypothesized that since CyaA-E7, CTX and CpG have different mechanisms of action, they could have a synergic effect. Thus, we administered CTX to 24 days tumor-bearing mice and 24 hour later, mice were injected with CyaA-E7 and CpG-B in DOTAP. This tritherapy showed a strong antitumor efficacy with a survival rate of 87.5%. Only two out of the sixteen mice receiving the tritherapy did not eradicate the tumor (FIG. 4 D, E). The CyaA-E7 vaccine was essential for this therapeutic effect since the administration of CTX and CpG-B/DOTAP was unable to induce the regression of the tumors, although this treatment induced a significant delay in the tumor growth as previously observed after the administration of CTX alone (FIGS. 4C, E).

To determine the potential of the tritherapy to cure very large tumors, we administered this treatment to tumor-bearing mice 30 or 40 days after tumor inoculation. When the tritherapy was administered on day 30, there was a decrease in the efficacy but still 41.7% of the animals were able to eradicate the tumor (FIGS. 5.1D, F). Even on day 40, when the tumor diameter ranged between 15 and 20 mm, two mice definitively eradicated the tumor. Remarkably, in all treated mice, tumors started to regress reflecting the induction of an effective immune response that last for around 20 days and was then followed by tumor relapse (FIGS. 5.1E, F). However, the regression phase could be prolonged by a second administration of the tritherapy at day 55, leading to tumor eradication in 43% of treated mice (FIG. 5.2).

To expand these results to another model of HPV-induced tumor, we injected mice subcutaneously with EL4 cells transfected with the E7 protein (EL4-E7 cells) (15). The growth of these cells was faster than the TC-1 growth and at day 14, EL4-E7 tumors reached a similar size to TC-1 tumors at day 30 (FIGS. 6A, E). Seven, 14 or 21 days after tumor cells injection, mice were treated by the tritherapy. As shown in FIG. 6, the tritherapy was effective to treat tumor until 14 days after inoculation but failed to eradicate the tumor 21 days after the inoculation. Similarly to the TC-1 model, all tumors started to regress but finally most of them relapsed.

Changes in Immune Cells During Tumor Development

We then investigated the mechanisms underlying the loss of therapeutic activity of CyaA-E7 in large-tumor bearing mice. In particular, we investigated whether expansion of regulatory T cells (Treg) and/or myeloid suppressor cells (MDSCs) could be responsible for such a decrease of CyaA-E7 activity. The percentage of these cell populations in the spleen, inguinal draining lymph nodes (DLN) and tumor was thus analyzed at different time points after the injection of TC-1 cells (FIG. 7).

A high percentage of CD4$^+$ CD25$^+$FoxP3$^+$ cells was found infiltrating the tumor at all time points analyzed, indicating a specific recruitment and/or expansion of these cells. This population also increased progressively in spleens and DLNs of tumor-bearing mice. This increase was faster in the DLN and by day 10, the difference with the inguinal lymph node before tumor inoculation was significant (10.8 vs 8.7%; p<0.05) and this difference further increased on day 25 (12.6 vs 8.7% p<0.01) and on day 40 (16.1 vs 8.7%; p<0.01). In the spleen, a significant difference was only detectable on day 40 (20.7 vs 11.0%; p<0.01).

A myeloid derived CD11b$^+$GR1$^+$ cell population increased progressively in the spleen of tumor-bearing animals and on day 40, a significant higher percentage of these cells was found in the spleens of tumor-bearing mice as compared to control mice (11.6 vs 1.0%; p<0.01). This population expressed the IL-4 receptor alpha chain (CD124), recently associated with immunosuppressive MDSCs (FIG. 11A) (36).

In conclusion, a marked expansion of Treg was observed inside the tumor and also systematically, although less marked in spleen and lymph nodes. The expansion of myeloid-derived suppressor cells CD11b$^+$GR1$^+$ cells was only detectable in spleens of late stage tumor-bearing mice.

Figure 8A:
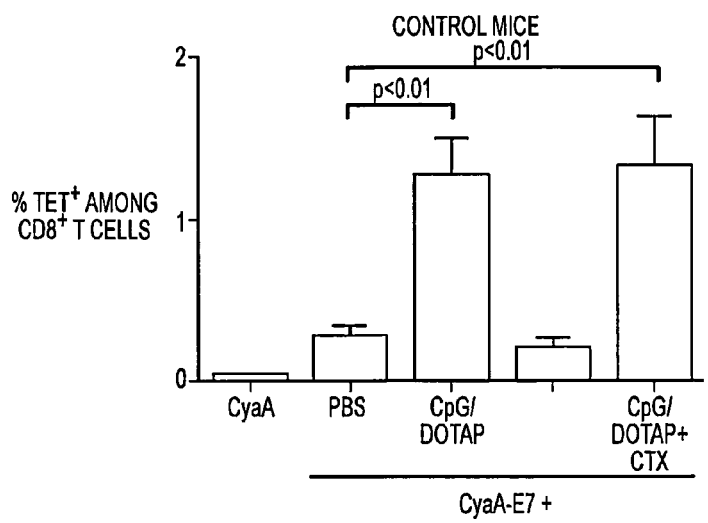

Analysis of Anti-Tumor Immune Responses Induced by the Tritherapy in Control and Tumor-Bearing Mice To study the immune responses induced by the different treatments, we analyzed the CD8$^+$ T cell response specific for the E7$_{49-57}$ CD8$^+$ T cell epitope by determining the percentage of tetramer$^+$ cells and the in vivo cytolytic activity generated in control and tumor-bearing mice. In control mice, the only treatment that significantly enhanced the number of tetramer$^+$ cells in comparison with the CyaA-E7 alone was the immunization with CpG-B/DOTAP and CyaA-E7 independent of the administration of CTX. Surprisingly, the tritherapy was less effective despite its stronger antitumor activity (FIG. 8A). In contrast, the in vivo CTL assay revealed a significant increase of cytolytic activity following immunization with both CyaA-E7+CpG-B/DOTAP or with the tritherapy.

Figure 8B:
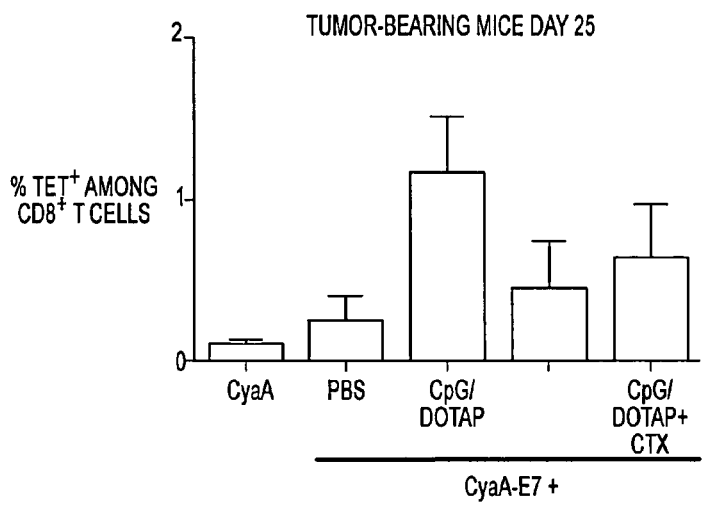
Figure 8C:
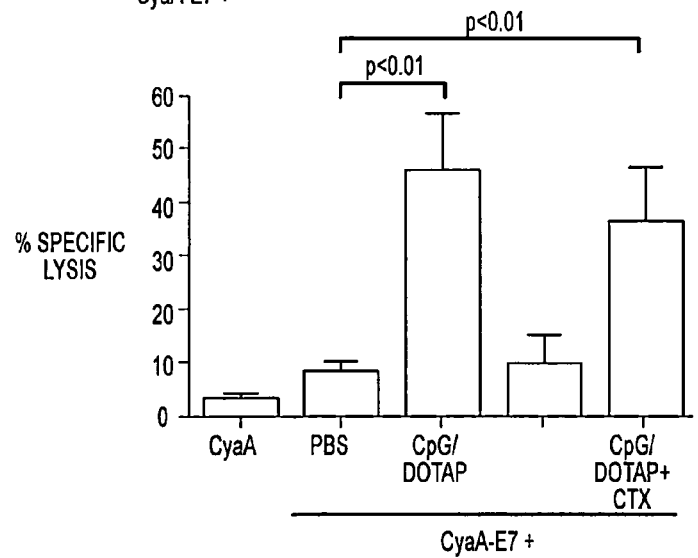
Figure 8D:
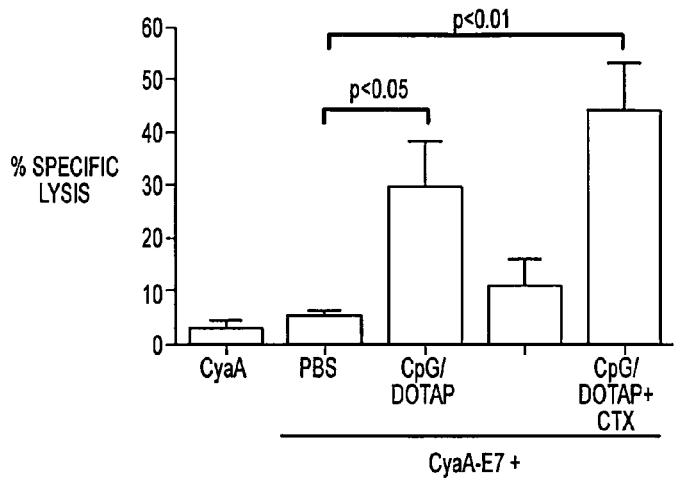

Mice grafted with TC-1 tumor cells 25 days before immunisation showed a lower increase in tetramer$^+$ cells than control immunized mice and none of the tested combinations was significantly different from immunization with CyaA-E7 alone (FIG. 8B). In contrast, a significantly stronger in vivo CTL activity was observed in mice immunized with CyaA-E7+CpG-B/DOTAP in the absence or presence of CTX ($p<0.05$) than with CyaA-E7 alone (FIG. 8D). The administration of CTX with CyaA-E7 did not enhance the immune response induced by CyaA-E7, despite its strong antitumor activity.

Figure 8E:
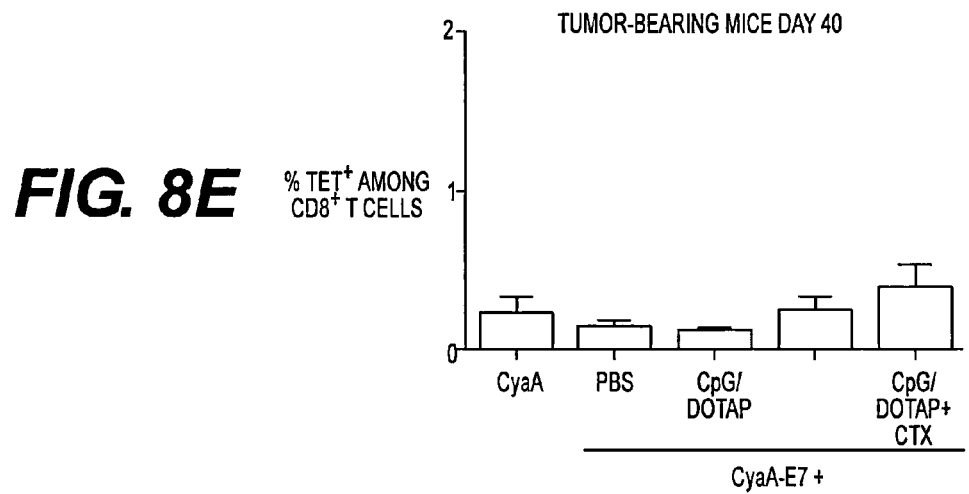
Figure 8F:
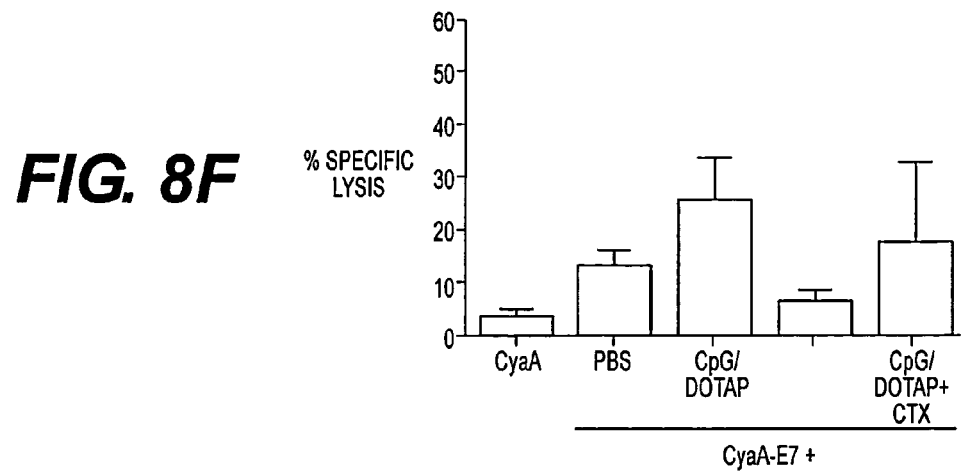

No tetramer$^+$ cells were detected in tumor-bearing mice 40 days after TC-1 injection. The in vivo cytolytic activity was low but still detected (FIG. 8E-F). Thus, the expansion of myeloid-derived suppressor cells and Treg associated with TC-1 growth gradually impairs the antitumor immune response induced by tritherapy. Moreover, in agreement with the antitumor data, in tumor-bearing mice, the tritherapy induced the highest in vivo cytotoxic activity of all combinations tested.

Changes in Immune Cells After Tritherapy on Day 25.

Next we evaluated the changes in the immune system induced by the tritherapy while the tumor is rejected. Specifically, we analyzed the evolution of the T regulatory cells, myeloid suppressor cells, tumor-specific CD8$^+$ T cells and NK cells.

As expected, the administration of cyclophosphamide induced a transient lymphodepletion in spleen and lymph node that reverted by day 7. The CD25$^+$FoxP3$^+$CD4$^+$ population showed a slightly more pronounced decrease than total CD4$^+$ cells, that did not reach statistical significance in the spleen and draining lymph node (FIG. 9). Interestingly enough, tumor-associated regulatory T cells experienced a significant decrease. The percentage of CD25$^+$FoxP3$^+$/CD4$^+$ cells dropped from 50% in non-treated mice to 30% on day 4 and 7 after treatment (FIG. 9A). Surprisingly, 11 days after the tritherapy, an increase of CD25$^-$FoxP3$^+$ cells was observed in all organs analyzed, leading to a significant increase in the percentage of FoxP3$^+$CD4$^+$ T cells in the spleen and draining lymph node and to a rapid recovery of regulatory T cells percentage in the tumors (FIGS. 9B, C). In parallel to these expansion of FoxP3$^+$ cells, a significant increase of tumor specific CD8$^+$ T cells was detected in the spleen, DLN and tumors, where the percentage of tetramer positive cells were especially high (FIG. 9D). Other evidences of the immune response onset were detected as, for instance, a transient activation of NK cells in spleen and DLN, further indicating the onset of the immune response. Anti-CD3 immunohistochemistry revealed a low T cell infiltration in non-treated tumors that increased dramatically 11 days after tritherapy. Tumors treated on day 40 presented a reduced T cell infiltration as compared to tumor treated on day 25 (FIG. 10).

We found a much higher percentage of CD11b$^+$GR1$^+$ cells (up to 30% of the cells) in the spleen of mice receiving tritherapy than in control mice. Though not as pronounced, there was also a higher percentage of CD11b$^+$GR1$^+$ cells in the DLN in mice receiving tritherapy than in controls (FIGS. 9F, G, H). This population expressed the specific granulocyte marker Ly6G but not the IL-4 receptor alpha chain. These markers identified this population as nonsuppressive granulocytes/neutrophils (FIG. 11). Finally, a strong increase in CD11b+GR1+ myeloid suppressor cells was observed in the spleen and more moderately in the DLN (FIGS. 9F, G, H).

Discussion

The aim of this work was to test combination treatments that could enhance the antitumor activity displayed by the recently developed CyaA-E7 therapeutic vaccine. This vaccine has the remarkable property to induce antitumor immunity in absence of any adjuvant but its effectiveness is abolished as the tumor progresses (FIG. 1). Our results point out that in order to display maximal activity of this vaccine, the innate immune system has to be activated and, simultaneously, the regulatory component of the immune system has to be down-regulated.

The activation of the innate immune system can be readily performed by synthetic TLR ligands. Nevertheless, not all the ligands performed well and we could detect differences even among ligands of the same TLR as in the case of the TLR-7 ligands, R848 and pU complexed with DOTAP. An explanation to this observation could be the different pharmacokinetic profile of a small molecule, R848, versus a liposomal formulation of an oligonucleotide, underscoring a fundamental dimension for the development of new adjuvants based of the TLR triggering. The best results were obtained with phosphorothioate CpG oligonucleotides complexed with DOTAP, reaching 50 to 60% of complete eradication of tumors treated 25 days after inoculation. In the rest of the tumors, a delay in the growth could be achieved but finally regrew. In this advance tumor model, the administration of the TLR ligands alone did not have any effect in the tumor growth. Therefore, the simultaneous administration of the CyaA-E7 was required to obtain a therapeutic effect.

A different approach tested was the synergy of immunotherapy and chemotherapy. We chose two widely used drugs, named cyclophosphamide and doxorubicin, that have been shown to enhance antitumor vaccine efficacy (21). Moreover, intratumoral injections of doxorubicin have been recently shown to induce an immunogenic cells death that lead to tumor immune rejection (22). However, in our model only cyclophosphamide had an adjuvant activity when combined with CyaA-E7, inducing the tumor regression in around 60% of treated mice. In contrast, doxorubicin had no effect when used either by intratumoral route or intravenously. A single injection of low dose of cyclophosphamide could transiently control tumor growth but was not able to induce the complete eradication. As in the case of the TLR ligands, the administration of CyaA-E7 was indispensable. Low dose of cyclophosphamide has been recently shown to decrease the number and inactivate Treg (13,23,24). In our model, a high percentage of CD25+FoxP3+ cells versus CD4+ cells was detected in tumor-infiltrated lymphocytes, and this percentage increased in the draining lymph node and spleen as tumor progress. Four days after the administration of cyclophosphamide, a slight decrease of these cells was detected in the spleen and draining lymph node, but the strongest decrease was found in the tumor-infiltrated lymphocyte, where the percentage of CD25+FoxP3+/CD4+ decreased from around 50% to below 30%, reflecting a higher susceptibility to the cyclophosphamide of the tumor-associated T regulatory cells (TA-Treg). The alteration of the TA-Treg homeostasis may be a key step in the disturbance of the tumor stroma cell interactions following CTX treatment (25). CTX treatment was indeed reported to modify the functional profile of tumor-infiltrating T cells, as shown by their inability to produce IFN-γ and to change IL-10-producing tumor-infiltrating macrophages into IFN-γ producers. This disturbance, although not enough to induce complete regression in our model, pave the way for the effector cells induced by the CyaA-E7. Therefore, it could be anticipated that treatments that enhance the effector cells induced by CyaA-E7, would synergize with the low dose cyclophosphamide. Indeed, the maximal response was achieved by the combination of low dose cyclophosphamide, CpG-B/DOTAP and the vaccination with CyaA-E7. The combination of CpG, CTX and a vaccine in the form of DC-derived exosomes, have been tested previously by Taieb et al. (23) for the treatment of bulky B16A2/gp100 tumors. In this model however, CpG did not enhance antitumor efficacy of DC-derived exosomes given in combination with CTX. In contrast to these results, we observed strong synergy between the three components, CyaA-E7, CpG-B/DOTAP and CTX, of tritherapy. This tritherapy was able to eradicate large, established tumor in 87% of animals treated 25 days after inoculation with tumors of a mean diameter of 8 mm. The efficacy was reduced when treating larger tumors but even in mice treated 40 days after inoculation, when the tumor mean diameter reached around 2 cm, all the tumor exhibit a transient size reduction, reflecting the induction of an effective immune response. Worthy of note, 2 out of 12 mice bearing these huge tumors completely eradicated them. Moreover, a second administration of the tritherapy 15 days after the first treatment lead to tumor eradication in 43% of treated mice. These results were further corroborated using a different tumor model, based on the inoculation of EL4 cells transfected with the E7 protein.

The analysis of the immune responses induced by the tritherapy showed that the CpG/DOTAP treatment is the only adjuvant tested that can increase significantly the E7-specific $CD8^+$ T cell response as compared to the CyaA-E7 alone. In tumor bearing animals this difference was reduced and, although that treatment still increased the percentage of tetramer$^+$ cells, the difference was not statistically significant. The administration of CTX with the CpG/DOTAP and the vaccine reduced the E7-specific $CD8^+$ T cell response, probably as a consequence of the systemic lymphodepletion. In contrast, the in vivo CTL activity remained at similar level that those of CpG/DOTAP or was even higher in tumor-bearing mice. Thus, the CTLs induced by the tritherapy displayed a higher killing activity in a per cell basis. The administration of CTX slightly increased the immune response in tumor-bearing animals but not in control mice. This increase was lower that that induced by CpG/DOTAP. Therefore, both treatments can enhance the antitumor activity of CyaA-E7 but clearly by different mechanism of action. An expansion of Treg after vaccination of tumor bearing host has been reported both in mice (26,27) and in human (28), underscoring the potential that therapeutic cancer vaccines could deepen tumor-specific T-cell tolerance. In our tumor model, in parallel to the strong antitumor immunity induced by the tritherapy that lead to the eradication tumor in around 90% of treated mice, an expansion of FoxP3+CD4+ was detected in the spleen and draining lymph node. In addition, the composition of the FoxP3+CD4+ compartment regarding the CD25 marker in the spleen, draining lymph node and tumor is altered after tritherapy, showing an increase in the CD25− cells. This may reflect the expansion of tumor induced regulatory CD25− CD4+ as previously reported in (27). It has been demonstrated that, on a cell per cell basis, $CD4^+$ $CD25^-$ $FoxP3^+$ cells are as regulatory as $CD4^+CD25^+FoxP3^+$ cells (31). We observed substantial expansion of neutrophils in the spleen and draining lymph node following tritherapy. As key component of the inflammatory response, neutrophils made important contributions to the recruitment, activation and programming of antigen presenting cells and contribute to the quality of the secondary immune response (33, 34). However, neutrophils expansion may detrimentally affect the on-going antitumor response by the secretion of reactive oxygen species (35).

Moreover, in spleen and draining lymph node, there were a huge expansion of CD11b+GR1+ myeloid suppressor cells, that may exert a detrimental impact on the on-going antitumor response directly by the secretion of NO (29) or indirectly by the simulation of T regulatory cells (30). Interestingly, these cells increased also in the spleen at the late stage of TC-1 growth where the tritherapy were not able to induce complete tumor regression. Thus, the cyclophosphamide only controls the regulatory component of immune system during the priming phase of the vaccine and the expansion of regulatory systems during the effector phase may be responsible, in part, of the abrogation of the effector immune response in mice immunized 40 days after tumor inoculation. Thus, new strategies to block the induction or to promote the inactivation of the regulatory component of the immune systems during the effector phase of the immune response should be evaluated, tipping the balance in favor of the effector function.

REFERENCES (1) Guermonprez P, Ladant D, Karimova G, Ullmann A, Leclerc C. Direct delivery of the *Bordetella pertussis* adenylate cyclase toxin to the MHC class I antigen presentation pathway. J Immunol 1999; 162:1910-6.
(2) Ladant D, Ullmann A. Bordatella pertussis adenylate cyclase: a toxin with multiple talents. Trends Microbiol 1999; 7:172-6.
(3) Schlecht G, Loucka J, Najar H, Sebo P, Leclerc C. Antigen targeting to CD11b allows efficient presentation of CD4+ and CD8+ T cell epitopes and in vivo Th1-polarized T cell priming. J Immunol 2004; 173:6089-97.
(4) Fayolle C, Ladant D, Karimova G, Ullmann A, Leclerc C. Therapy of murine tumors with recombinant *Bordetella pertussis* adenylate cyclase carrying a cytotoxic T cell epitope. J Immunol 1999; 162:4157-62.
(5) Preville X, Ladant D, Timmerman B, Leclerc C. Eradication of established tumors by vaccination with recombinant *Bordetella pertussis* adenylate cyclase carrying the human papillomavirus 16 E7 oncoprotein. Cancer Res 2005; 65:641-9.
(6) Lowndes CM. Vaccines for cervical cancer. Epidemiol Infect 2006; 134:1-12.

(7) Bosch F X, Lorincz A, Munoz N, Meijer C J, Shah K V. The causal relation between human papillomavirus and cervical cancer. J Clin Pathol 2002; 55:244-65.

(8) Munger K, Phelps W C, Bubb V, Howley P M, Schlegel R. The E6 and E7 genes of the human papillomavirus type 16 together are necessary and sufficient for transformation of primary human keratinocytes. J Virol 1989; 63:4417-21.

(9) von Knebel Doeberitz M, Rittmuller C, zur Hausen H, Durst M. Inhibition of tumorigenicity of cervical cancer cells in nude mice by HPV E6-E7 anti-sense RNA. Int J Cancer 1992; 51:831-4.

(10) Hopfl R, Heim K, Christensen N, Zumbach K, Wieland U, Voigger B, et al. Spontaneous regression of CIN and delayed-type hypersensitivity to HPV-16 oncoprotein E7. Lancet 2000; 356:1985-6.

(11) Akira S, Takeda K. Toll-like receptor signalling. Nat Rev Immunol 2004; 4:499-511.

(12) Yang S, Haluska F G. Treatment of melanoma with 5-fluorouracil or dacarbazine in vitro sensitizes cells to antigen-specific CTL lysis through perforin/granzyme- and Fas-mediated pathways. J Immunol 2004; 172:4599-608.

(13) Lutsiak M E, Semnani R T, De Pascalis R, Kashmiri S V, Schlom J, Sabzevari H. Inhibition of CD4(+)25+ T regulatory cell function implicated in enhanced immune response by low-dose cyclophosphamide. Blood 2005; 105:2862-8.

(14) Lin K Y, Guarnieri F G, Staveley-O'Carroll K F, Levitsky H I, August J T, Pardoll D M, et al. Treatment of established tumors with a novel vaccine that enhances major histocompatibility class II presentation of tumor antigen. Cancer Res 1996; 56:21-6.

(15) Tindle R W, Croft S, Herd K, Malcolm K, Geczy A F, Stewart T, et al. A vaccine conjugate of 'ISCAR' immunocarrier and peptide epitopes of the E7 cervical cancer-associated protein of human papillomavirus type 16 elicits specific Th1- and Th2-type responses in immunized mice in the absence of oil-based adjuvants. Clin Exp Immunol 1995; 101:265-71.

(16) Feltkamp M C, Smits H L, Vierboom M P, Minnaar R P, de Jongh B M, Drijfhout J W, et al. Vaccination with cytotoxic T lymphocyte epitope-containing peptide protects against a tumor induced by human papillomavirus type 16-transformed cells. Eur J Immunol 1993; 23:2242-9.

(17) El Halimi R, Ocaña J, Ruiz de Villa M, Escrich E, Solanas M. Modelling tumor growth data using a non-linear mixed-effects model. InterStat 2003; http://interstat.statjournals.net/.

(18) Li Q, Normolle D P, Sayre D M, Zeng X, Sun R, Jiang G, et al. Immunological effects of BCG as an adjuvant in autologous tumor vaccines. Clin Immunol 2000; 94:64-72.

(19) Facciabene A, Aurisicchio L, La Monica N. Baculovirus vectors elicit antigen-specific immune responses in mice. J Virol 2004; 78:8663-72.

(20) Berd D, Maguire H C, Jr., Mastrangelo M J. Induction of cell-mediated immunity to autologous melanoma cells and regression of metastases after treatment with a melanoma cell vaccine preceded by cyclophosphamide. Cancer Res 1986; 46:2572-7.

(21) Machiels J P, Reilly R T, Emens L A, Ercolini A M, Lei R Y, Weintraub D, et al. Cyclophosphamide, doxorubicin, and paclitaxel enhance the antitumor immune response of granulocyte/macrophage-colony stimulating factor-secreting whole-cell vaccines in HER-2/neu tolerized mice. Cancer Res 2001; 61:3689-97.

(22) Casares N, Pequignot M O, Tesniere A, Ghiringhelli F, Roux S, Chaput N, et al. Caspase-dependent immunogenicity of doxorubicin-induced tumor cell death. J Exp Med 2005; 202:1691-701.

(23) Taieb J, Chaput N, Schartz N, Roux S, Novault S, Menard C, et al. Chemoimmunotherapy of tumors: cyclophosphamide synergizes with exosome based vaccines. J Immunol 2006; 176:2722-9.

(24) Ercolini A M, Ladle B H, Manning E A, Pfannenstiel L W, Armstrong T D, Machiels J P, et al. Recruitment of latent pools of high-avidity CD8(+) T cells to the antitumor immune response. J Exp Med 2005; 201:1591-602.

(25) Ibe S, Qin Z, Schuler T, Preiss S, Blankenstein T. Tumor rejection by disturbing tumor stroma cell interactions. J Exp Med 2001; 194:1549-59.

(26) Maksimow M, Miiluniemi M, Marttila-Ichihara F, Jalkanen S, Hanninen A. Antigen targeting to endosomal pathway in dendritic cell vaccination activates regulatory T cells and attenuates tumor-immunity. Blood 2006.

(27) Zhou G, Drake C G, Levitsky H I. Amplification of tumor-specific regulatory T cells following therapeutic cancer vaccines. Blood 2006; 107:628-36.

(28) Banerjee D, Dhodapkar M V, Matayeva E, Steinman R M, Dhodapkar K. Expansion of FOXP3high regulatory T cells by human dendritic cells (DCs) in vitro and after DC injection of cytokine matured DCs in myeloma patients. Blood 2006.

(29) Angulo I, de las Heras F G, Garcia-Bustos J F, Gargallo D, Munoz-Fernandez M A, Fresno M. Nitric oxide-producing CD11b(+)Ly-6G(Gr-1)(+)CD31(ER-MP12)(+) cells in the spleen of cyclophosphamide-treated mice: implications for T-cell responses in immunosuppressed mice. Blood 2000; 95:212-20.

(30) Yang R, Cai Z, Zhang Y, Yutzy I V W, Roby K, Roden R. CD80 in Immune Suppression by Mouse Ovarian Carcinoma-Associated Gr-1+CD11b+ Myeloid Cells. Cancer Res 2006; 66:6807-15.

(31) Nava-Parada, P. Formi G, Knutson K L, Pease L R, Celis E. Peptide vaccine given with a Toll-like receptor agonist is effective for the treatment and prevention of spontaneous breast tumors. Cancer Res 2007; 67(3): 1326-34.

(32) Banerjee D, Dhodapkar M V, Matayeva E, Steinman R M, Dhodapkar K. Expansion of FOXP3high regulatory T cells by human dendritic cells (DCs) in vitro and after DC injection of cytokine matured DCs in myeloma patients. Blood 2006; 108: 1298-305.

(33) Bennouna S, Bliss S K, Curiel T J, Denkers E Y. Cross-talk in the innate immune system: neutrophils instruct recruitment and activation of dendritic cells during microbial infection. J. Immunol. 2003; 171(11): 6052-8.

(34) Maletto B A, Ropolo A S, Alignani D O, et al. Presence of neutrophil-bearing antigen in lymphoid organs of immune mice. Blood 2006; 108(9): 3094-102.

(35) Schmielau J, Finn O J. Activated granulocytes and granulocyte-derived hydrogen peroxide are the underlying mechanism of suppression of t-cell function in advanced cancer patients. Cancer Res 2001; 61(12): 4756-60.

(36) Gallina G, Dolcetti L, Serafini P, et al. Tumors induce a subset of inflammatory monocytes with immunosuppressive activity on CD8+ T cells. The Journal of clinical investigation 2006; 116(10):2777-90.

The invention claimed is:

1. A kit of parts comprising compounds for antitumor therapy in a host, wherein said compounds comprise:
   (i) a recombinant adenylate cyclase (CyaA) protein or fragment thereof, the CyaA protein or fragment thereof comprising at least one inserted polypeptide bearing at least one epitope of a tumor-associated antigen, wherein the CyaA protein or fragment thereof retains the ability to target the CD11b/CD18 receptor on Antigen Presenting Cells; and
   (ii) a toll-like receptor (TLR) agonist selected from a TLR-9 agonist, a TLR-3 agonist, and a TLR-7 agonist, wherein the recombinant adenylate cyclase (CyaA) protein or fragment thereof, and the TLR agonist are in amounts sufficient to reduce the growth of a tumor in the host.

2. The kit of parts of claim 1, wherein TLR agonist is a TLR-9 agonist.

3. The kit of parts of claim 2, wherein the TLR-9 agonist is a type A CpG oligonucleotide and/or a type B CpG oligonucleotide.

4. The kit of parts of claim 1, wherein the TLR agonist is a TLR-3 agonist.

5. The kit of parts of claim 4, wherein the TLR-3 agonist is a polyinosinic-polycytidylic acid (PIC).

6. The kit of parts of claim 1, wherein the TLR agonist is a TLR-7 agonist.

7. The kit of parts of claim 6, wherein the TLR-7 agonist is polyuridine (pU).

8. The kit of parts of claim 1, further comprising a chemotherapeutic agent.

9. The kit of parts of claim 2, further comprising a chemotherapeutic agent.

10. The kit of parts of claim 3, further comprising a chemotherapeutic agent.

11. The kit of parts of claim 4, further comprising a chemotherapeutic agent.

12. The kit of parts of claim 5, further comprising a chemotherapeutic agent.

13. The kit of parts of claim 6, further comprising a chemotherapeutic agent.

14. The kit of parts of claim 7, further comprising a chemotherapeutic agent.

15. The kit of parts of claim 8, wherein the chemotherapeutic agent is cyclophosphamide.

16. The kit of parts of claim 9, wherein the chemotherapeutic agent is cyclophosphamide.

17. The kit of parts of claim 10, wherein the chemotherapeutic agent is cyclophosphamide.

18. The kit of parts of claim 11, wherein the chemotherapeutic agent is cyclophosphamide.

19. The kit of parts of claim 12, wherein the chemotherapeutic agent is cyclophosphamide.

20. The kit of parts of claim 13, wherein the chemotherapeutic agent is cyclophosphamide.

21. The kit of parts of claim 14, wherein the chemotherapeutic agent is cyclophosphamide.

22. The kit of parts of claim 1, wherein the kit of parts comprises a plurality of recombinant adenylate cyclase (CyaA) proteins or fragments thereof, each recombinant CyaA protein or fragment thereof comprising at least one inserted polypeptide bearing at least one epitope of a tumor-associated antigen, wherein the plurality of CyaA proteins or fragments thereof retain the ability to target the CD11b/CD18 receptor on Antigen Presenting Cells.

23. The kit of parts of claim 1, wherein the recombinant CyaA protein or fragment thereof comprises from about 30 to about 1300 amino acid residues of the CyaA protein of *Bordetella pertussis*, wherein the about 30 to about 1300 amino acid residues comprise at least one fragment selected from amino acid residues 1208 to 1243 of the CyaA protein of *Bordetella pertussis* or amino acid residues 1166 to 1281 of the CyaA protein of *Bordetella pertussis*.

24. The kit of parts of claim 1, wherein the recombinant CyaA protein or fragment thereof is the full-length CyaA protein of *Bordetella pertussis* comprising one or several polypeptides inserted at the position between codons 224 and 225.

25. The kit of parts of claim 1, wherein the tumor associated antigen is a tumor associated antigen of an oncogenic HPV selected from HPV16, HPV18, HPV31, HPV33, HPV35, HPV45, HPV52 and HPV58.

26. The kit of parts of claim 1, wherein the tumor associated antigen is selected from the E6 protein of HPV16, the E6 protein of HPV18, the E7 protein of HPV16, and the E7 protein of HPV18.

27. The kit of parts of claim 1, wherein the recombinant CyaA protein or fragment thereof comprises a plurality of inserted polypeptides each bearing at least one epitope of a tumor-associated antigen and inserted at a different permissive site of the CyaA protein or fragment thereof.

28. The kit of parts of claim 27, wherein the plurality of inserted polypeptides comprise a fragment comprising residues 1 to 29 of E7 protein of HPV16, a fragment comprising residues 43 to 98 of E7 protein of HPV16, or both fragments.

29. The kit of parts of claim 1, wherein the at least one inserted polypeptide is selected from RAHYNIVTF (SEQ ID NO: 1) ($E7_{49-57}$), GQAEPDRAHYNIVTFCCKCDSTLRL-CVQSTHVDIR (SEQ ID NO: 2) ($E7_{43-77}$), and (I/A) (D/S) GVNHQHL (SEQ ID NO: 4).

30. The kit of parts of claim 1, wherein the recombinant CyaA protein or fragment thereof is the CyaA protein of *Bordetella pertussis* comprising one or several polypeptides inserted at the position between codons 224 and 235.

31. The kit of parts of claim 30, wherein residues 225 to 234 of the CyaA protein of *Bordetella pertussis* are deleted.

32. The kit of parts of claim 22, wherein the kit of parts comprises
   A) a first recombinant adenylate cyclase (CyaA) protein comprising:
      amino acid residues 43 to 98 of HPV16-E7 inserted at a first insertion site within the first CyaA protein; and amino acid residues 1 to 29 of HPV16-E7 inserted at a second insertion site within the first CyaA protein; and B) a second recombinant adenylate cyclase (CyaA) protein comprising:

amino acid residues 43 to 105 of HPV 18-E7 inserted at a first insertion site within the second CyaA protein; and amino acid residues 1 to 31 of HPV 18-E7 inserted at a second insertion site within the second CyaA protein.

* * * * *